United States Patent [19]
Chuter

[11] Patent Number: 5,387,235
[45] Date of Patent: Feb. 7, 1995

[54] EXPANDABLE TRANSLUMINAL GRAFT PROSTHESIS FOR REPAIR OF ANEURYSM

[75] Inventor: Timothy A. Chuter, Pittsford, N.Y.

[73] Assignee: Cook Incorporated, Bloomington, Ind.

[21] Appl. No.: 959,758

[22] Filed: Oct. 21, 1992

Related U.S. Application Data

[63] Continuation-in-part of Ser. No. 868,795, Apr. 19, 1992, abandoned, which is a continuation-in-part of Ser. No. 782,696, Oct. 25, 1991, abandoned.

[51] Int. Cl.$^6$ .......................... A61F 2/06; A61F 2/04; A61M 29/02; A61M 29/00
[52] U.S. Cl. ......................................... 623/1; 623/12; 606/194; 604/96
[58] Field of Search ............................... 623/1, 11, 12; 606/191–200; 600/36; 604/96

[56] References Cited

U.S. PATENT DOCUMENTS

| | | | |
|---|---|---|---|
| 3,657,744 | 4/1972 | Ersek | 3/1 |
| 4,140,126 | 2/1979 | Choudhury | 128/325 |
| 4,512,338 | 4/1985 | Balko et al. | 128/1 |
| 4,577,631 | 3/1986 | Kreamer | 128/334 |
| 4,580,568 | 4/1986 | Gianturco | 128/345 |
| 4,655,771 | 4/1987 | Wallsten | 623/1 |
| 4,733,665 | 3/1988 | Palmaz | 128/343 |
| 4,739,762 | 4/1988 | Palmaz | 128/343 |
| 4,740,207 | 4/1988 | Kreamer | 623/1 |
| 4,776,337 | 10/1988 | Palmaz | 128/343 |
| 4,787,899 | 11/1988 | Lazarus | 623/1 |
| 4,830,003 | 5/1989 | Wolff et al. | 128/343 |
| 4,913,141 | 4/1990 | Hillstead | 606/194 |
| 5,035,706 | 7/1991 | Gianturco et al. | 606/198 |
| 5,104,399 | 4/1992 | Lazarus | 623/1 |

OTHER PUBLICATIONS

Cragg, A. H. et al., "Percutaneous Arterial Grafting", *Radiology*, vol. 150, No. 1, Jan. 1984, pp. 45–49.
Matsumae, M. et al., "An Experimental Study of a New Sutureless Intraluminal Graft With an Elastic Ring That Can Attach Itself to the Vessel Wall", *Journal of Vascular Surgery*, vol. 8, No. 1, Jul. 1988, pp. 38–44.
Mirich, D. et al., "Percutaneously Placed Endovascular Grafts for Aortic Aneurysms: Feasibility Study", *Radiology*, vol. 170, No. 3, Part 2, Mar. 1989, pp. 1033–1037.
Maass, D. et al., "Radiological Follow-up of Transluminally Inserted Vascular Endoprostheses: An Experimental Study Using Expanding Spirals", *Radiology*, vol. 152, No. 3, 1984, pp. 659–663.
Richter, G. M. et al., "Three-year Results of Use of Transjugular Intrahepatic Portosystemic Stent Shunt", R.S.N.A. 1991 Abstracts, p. 99, No. 63.
Richter, G. M. et al., "Superior Clinical Results of Iliac Stent Placement versus Percutaneous Transluminal Angioplasty: Four-year Success Rates of Randomized Study", R.S.N.A. 1991 Abstracts, p. 161, No. 411.

(List continued on next page.)

Primary Examiner—Randall L. Green
Assistant Examiner—Debra Brittingham
Attorney, Agent, or Firm—Richard J. Godlewski

[57] ABSTRACT

A transluminal arrangement for positioning a prosthesis assembly at an aneurysm in the bifurcated lumen of the aorta and the common iliac arteries extending therefrom. The prosthesis assembly includes a bifurcated endovascular graft having a main body and ipsilateral and contralateral limbs extending therefrom. The assembly also includes main, ipsilateral, and contralateral spring assemblies each having a compressed state. When released from its compressed state, each spring expands a portion of the graft to substantially conform that portion of the graft to the wall of the bifurcated lumen. The transluminal arrangement comprises an elongated member extending through the main and ipsilateral bores of the graft and includes attachment sutures and an inner catheter extending therethrough for temporarily attaching the main and ipsilateral spring assemblies to the elongated member. An outer sheath contains the attached prosthesis assembly, whereas stent boots consisting of short length sheaths contain the ipsilateral and contralateral spring assemblies. A control limb delivery catheter and attachment sutures maintain the contralateral graft limb and spring assembly in the stent boot for placement in the contralateral iliac artery.

17 Claims, 23 Drawing Sheets

OTHER PUBLICATIONS

Vallbracht, C. et al., "New PTFE Closed Stent: First Experimental Results", R.S.N.A. 1991 Abstracts, p. 161, No. 415C.

Wunderlich, C. C. et al., "Imaging of the Palmaz Stent in the Prostatic Urethra", R.S.N.A. 1991 Abstracts, p. 217, No. 734C.

Palmaz, J. C. et al., "Three-year Experience with Iliac Artery Stents", R.S.N.A. 1991 Abstracts, p. 244, No. 894.

Lawrence, David D., Jr. et al., "Percutaneous Endovascular Graft: Experimental Evaluation," *Radiology*, vol. 163, No. 2, pp. 357–360, May 1987.

Palmaz, Julio C. et al., "Expandable Intraluminal Vascular Graft: A Feasibility Study," *Surgery*, vol. 99, No. 2, pp. 199–205, Feb. 1986.

Dotter, Charles T. et al., "Transluminal Expandable Nitinol Coil Stent Grafting: Preliminary Report," *Radiology*, vol. 147, pp. 259–260, Apr. 1983.

Cragg, Andrew et al., "Nonsurgical Placement of Arterial Endoprostheses: A New Technique Using Nitinol Wire," *Radiology*, vol. 147, pp. 261–263, Apr. 1983.

Dotter, Charles T., "Transluminally-placed Coilspring Endarterial Tube Grafts," *Invesigative Radiology*, vol. 4, No. 5, pp. 329–332, Sep.–Oct. 1969.

Palmaz, Julio C. t al., "Transluminal Bypass of Experimental Abdominal Aortic Aneurysm," R.S.N.A. 1990 Abstracts, p. 202, No. 695.

Carrasco, C. Humberto et al., "Gianturco Stent in Vena Caval Stenoses," R.S.N.A. 1990 Abstracts, p. 202, No. 696.

Inoue, Kanji et al., "Percutaneous Implantation of Aortic Endovascular Graft for Created Aneurysm: Animal Experiment," *Circulation* 1991, 84 (4 Suppl. II):II–421.

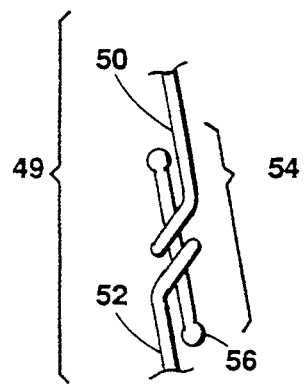
Fig. 7
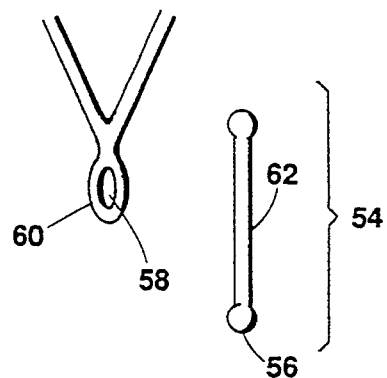
Fig. 8
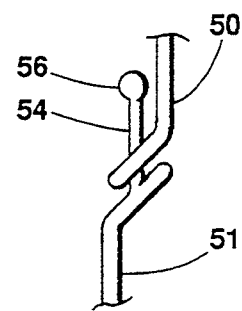
Fig. 10
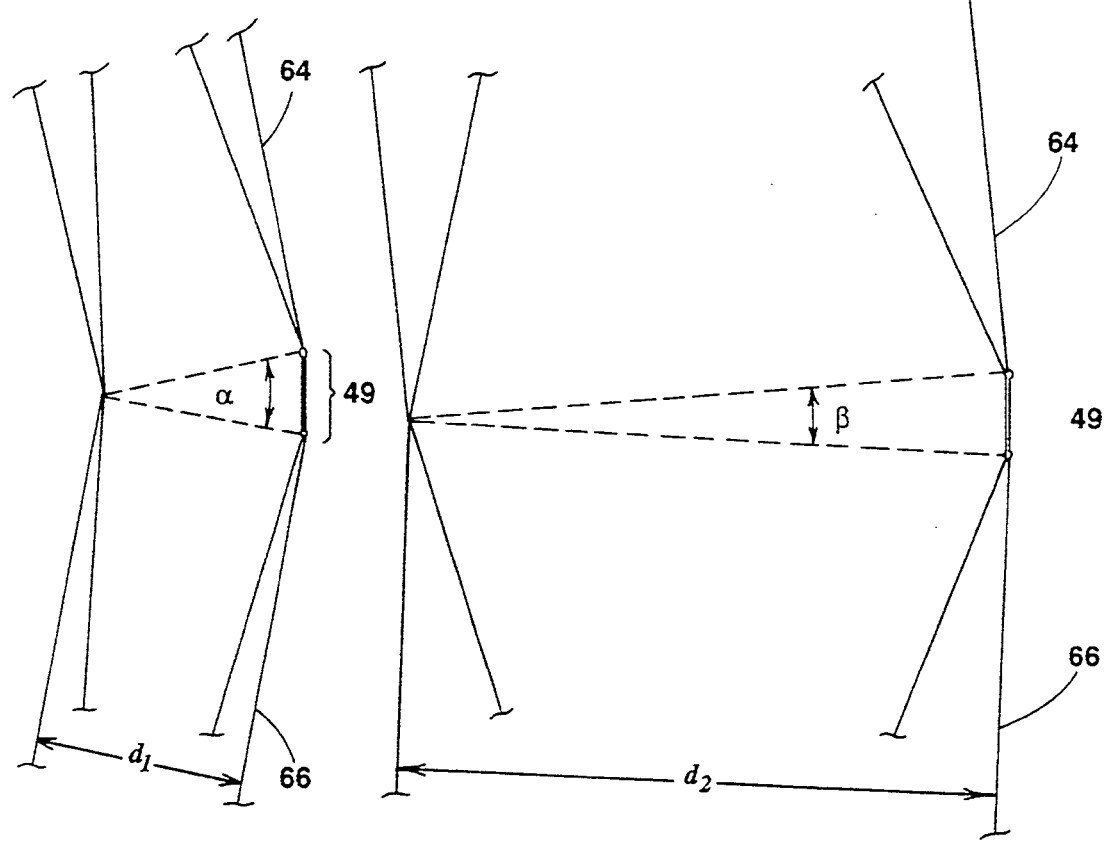
Fig. 9A
Fig. 9B

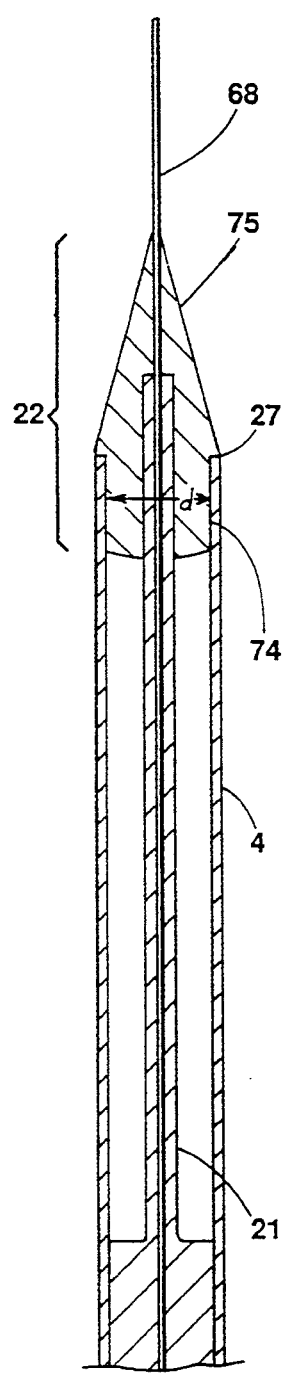
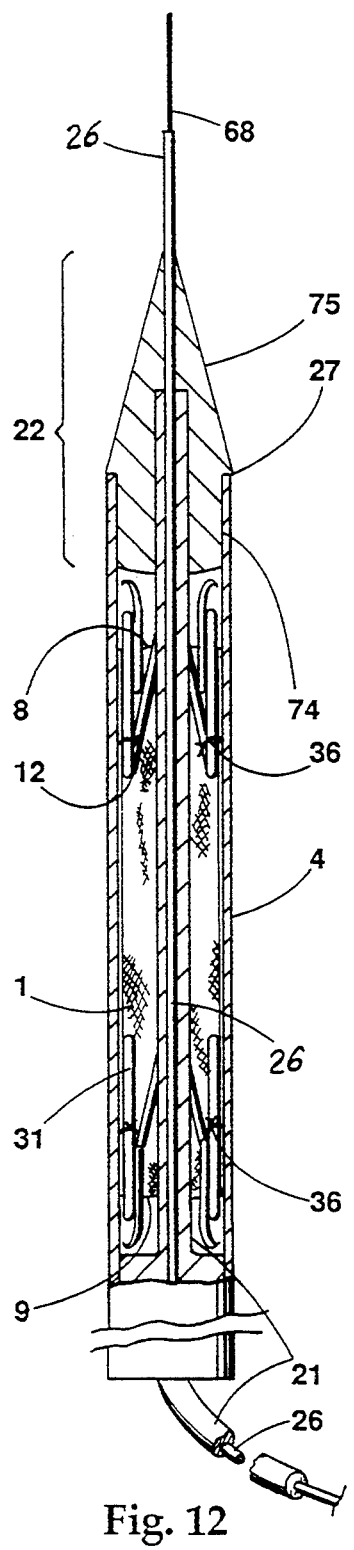
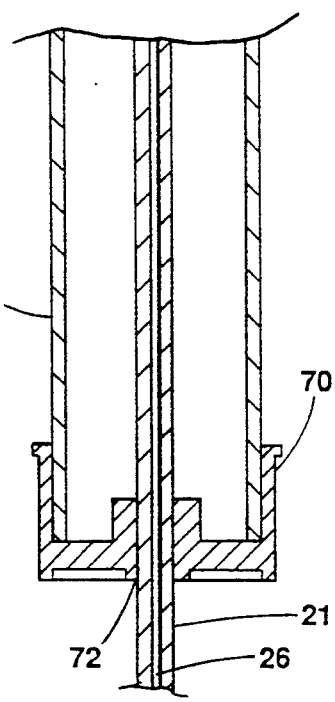
Fig. 11
Fig. 12
Fig. 13

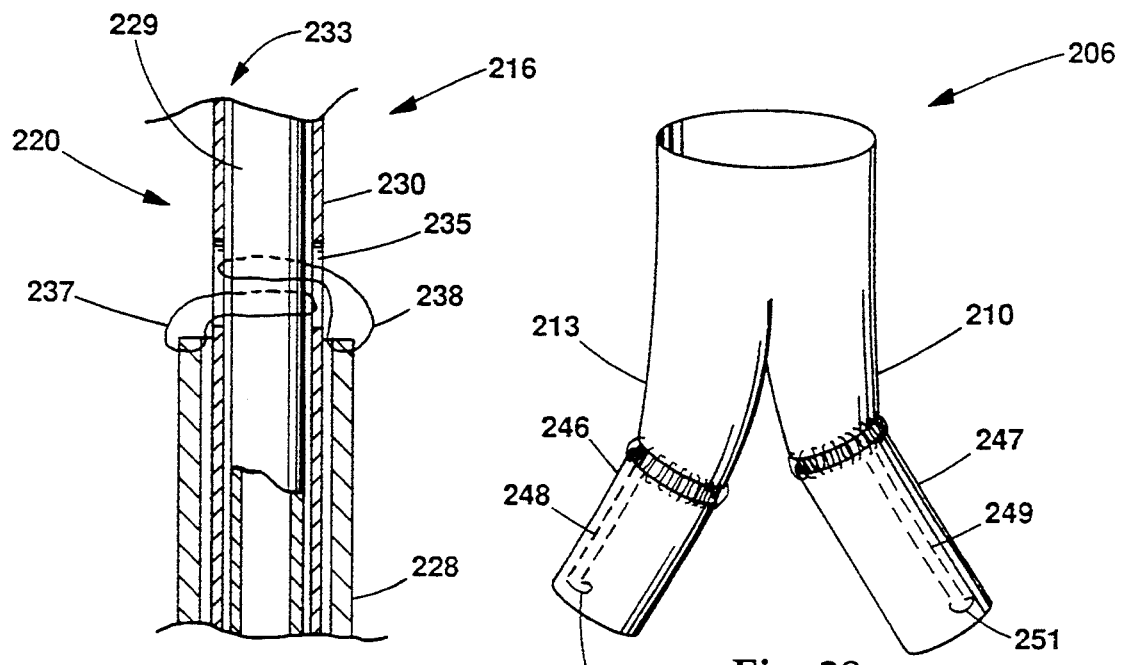
Fig. 27
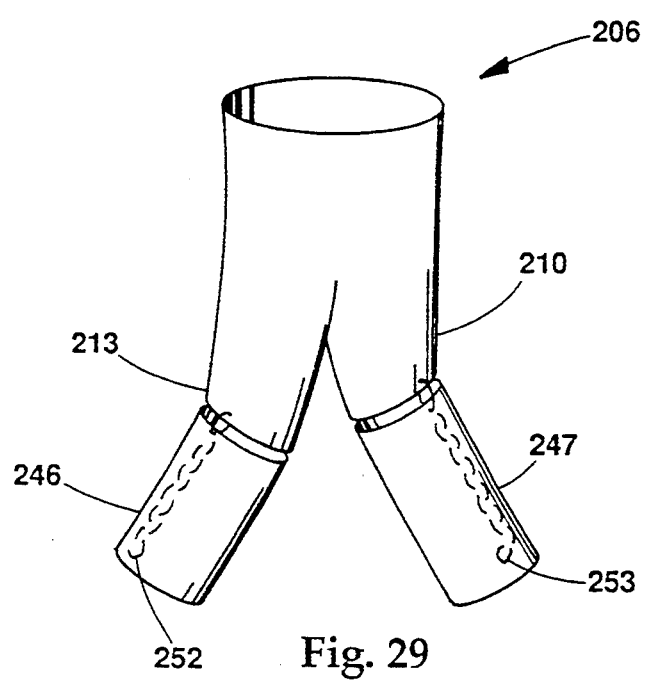
Fig. 28
Fig. 29

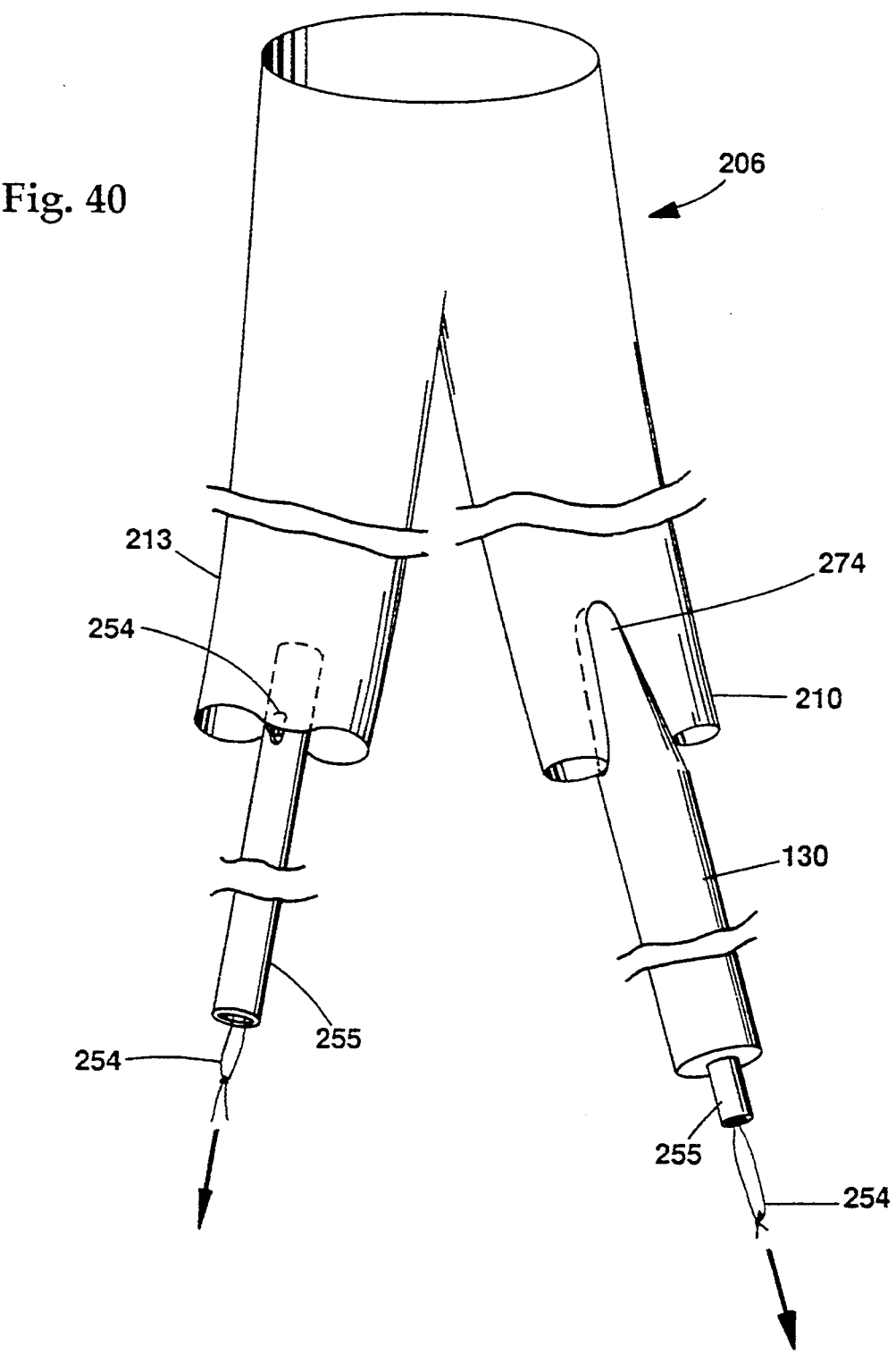

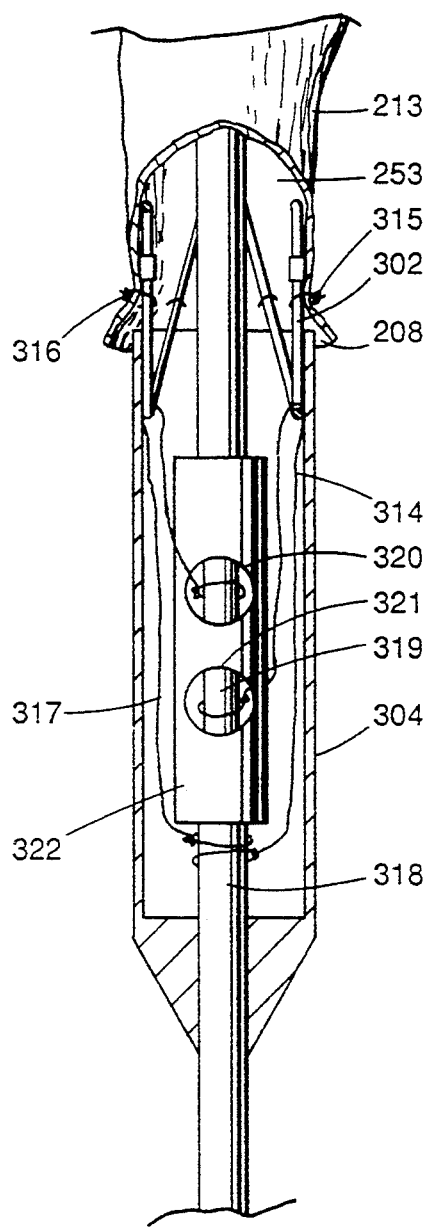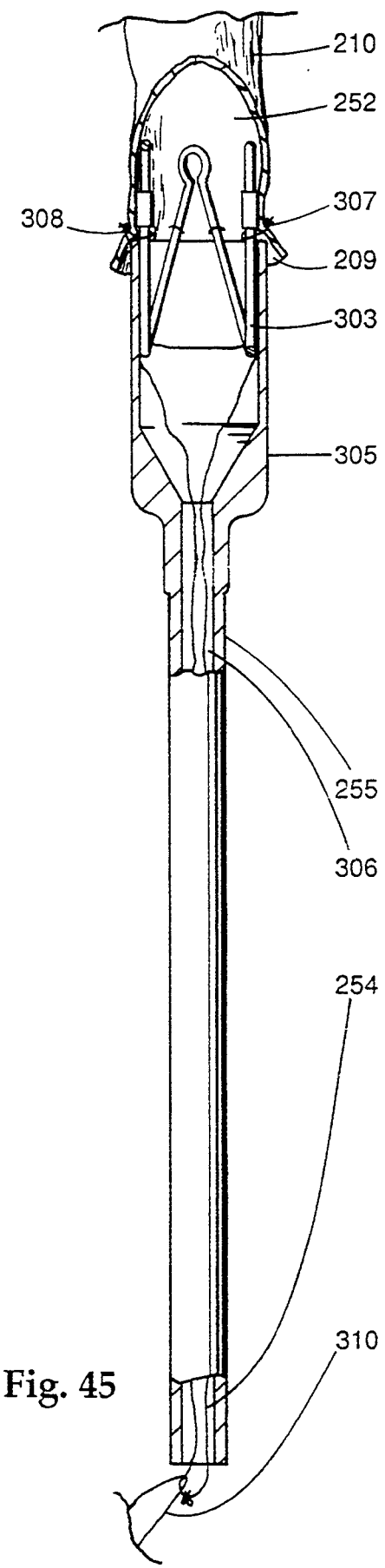
Fig. 44
Fig. 45

EXPANDABLE TRANSLUMINAL GRAFT PROSTHESIS FOR REPAIR OF ANEURYSM

CROSS-REFERENCE TO RELATED APPLICATIONS

This application is a continuation-in-part of application Ser. No. 07/868,795, filed on Apr. 15, 1992, which is a continuation-in-part of application Ser. No. 07/782,696, filed on Oct. 25, 1991, both now abandoned.

TECHNICAL FIELD

The invention relates to transluminal graft prostheses for the repair of aneurysms and a method for implanting them.

BACKGROUND OF THE INVENTION

The abdominal aorta is prone to aneurysmal dilation between the renal and iliac arteries. The attenuated wall of the aneurysm is unable to withstand arterial pressures so that dilation tends to progress to a point where rupture is likely. The highly invasive procedure necessary for conventional repair of an aortic aneurysm consists of an abdominal incision, dissection of the arteries, and the interruption of blood flow to the lower body and legs while an artificial graft is implanted to bypass the aneurysm.

Such invasive surgical repair of vital lumens has profound undesirable effects on the respiratory and cardiovascular systems of elderly patients who typically require the operation. The operation is expensive and entails significant life threatening risk. It is therefore highly desirable to replace conventional surgical repair with a less traumatic, less complicated and safer procedure. The present invention serves these needs, and is particularly well adapted to reconstruction of an abdominal aortic aneurysm. The prosthetic graft of this invention will provide a resilient conduit, bridging the aneurysm and reducing the risk of rupture, without the attendant morbidity and expense of conventional surgical repair. The invention, however, is not limited to aortic aneurysm repair and has applications in a variety of situations in which corporeal lumen repair is required.

There are several devices already existing which are stated to be useful for the remote repair of corporeal lumens. U.S. Pat. No. 4,512,338, issued to Balko et al., discloses a device for transluminal repair of, and restoring patency of, a weakened or damaged corporeal vessel. The device consists of a nitinol wire, previously memory-shaped into a longitudinal coil, which is cooled and reformed into a straight wire and inserted into the vessel requiring repair. When placed in the body and stripped of heat insulating means, the wire warms and returns to its preselected coiled dimensions to support the vessel wall. Use of a device such as nitinol wire may be undesirable because there is a danger of possibly puncturing or lacerating the lumen wall during the emplacement process. Another problem lies in fitting the prostheses to the vessel because the prosthesis does not assume its final shape (and length) until it is inside the artery. The exact position of both ends of the prostheses is very important due to the proximity of vital arteries to the ends of the aneurysm. Yet another problem with these devices is the difficult task of attaching the sleeve to the wire support because the wire is many times longer than the sleeve at the time it is inserted.

U.S. Pat. No. 4,140,126, issued to Choudhury, discloses a device for repairing an aneurysm. The device is mounted on the outside of a carrier catheter, and is positioned in the vessel in a collapsed form, smaller in diameter than that of the vessel. The device is then expanded onto the vessel wall by means of a mechanical expanding apparatus which is controlled by the user from outside the body by means of a wire. Upon expansion, anchoring pins are driven into the vessel wall. The wire is positioned on the outside of the carrier catheter, and is held in place by passing through many slip rings, each of which is firmly attached to the catheter. The slip rings permit the wire to slide when remotely operated. The wire is also attached to the expanding means at its proximal (downstream) end by slip couplings which permit the wire and expansion means to pass through the couplings during the expansion process. This device is mechanically complex and may not apply sufficient force to drive the pins into an atherosclerotic aorta or seal the graft to the arterial lumen. Furthermore, there is nothing to shield the vessel wall from the sharp pins while the device is moving from the insertion point to the point of repair. The pins are interspaced in folds of the graft material and could protrude from these folds while the device is moved into position. This could result in damage to the vessel wall in locations remote from the repair.

U.S. Pat. No. 4,787,899, issued to Lazarus, describes a system of positioning a graft within a body lumen. The graft is loaded into a guide which is inserted into the lumen. An inflatable balloon is used to anchor the distal (upstream) end of the graft onto the wall of the lumen, and then the guide is pushed upstream, pulling the folded graft out of the guide and onto the wall of the lumen, where staples at the proximal (downstream) end anchor into the wall of the lumen. Because the graft is folded or crimped axially, there is no sure method of determining where the expanded graft will position itself on the wall of the lumen, other than by measuring from the point of initial contact on the wall. This is difficult to do utilizing the remote insertion procedure. Also, the balloon providing the anchor for the distal (upstream) end of the graft while the guide is moved upstream may not provide enough pressure on the wall of the vessel to prevent slippage which could result in misplacement of the graft. The axial crimping used in these grafts may not impart radial elasticity and standard graft materials may not have sufficient elasticity as an intrinsic property. The small amount of apparent elasticity present in knitted grafts is actually a form of deformability in that expansion in one direction is accompanied by contraction in another. This means that the "guide" should be very close in size to the lumen of the vessel. As such, it should be introduced directly into the vessel to be repaired, rather than via a distant (much smaller) vessel. Also, the large guide may be difficult to withdraw through the graft after placement since it presents an open edge which might catch on any irregularities of the lumen.

The report, *Percutaneously Placed Endovascular Grafts for Aortic Aneurysms: Feasibility Study*, from the Department of Diagnostic Radiology, University of Texas M. D. Anderson Cancer Center, printed in 170 Radiology 1033–37 (1989), deals with a self-expanding graft consisting of several stents connected in a chain. Two stainless steel struts run down the length of the chain, forming a rigid structure along the longitudinal axis. The structure is partially covered in a secured nylon sheath, is compressed radially, and is introduced into a lumen via a catheter and a blunt-tipped introducer wire used to push the graft up the catheter and into position. Placement is secured by withdrawing the catheter while holding the introducer wire stationary. This device may be difficult to insert because a chain structure is difficult to push unless it is rigid. The rigidity would make it very difficult to negotiate femoral and iliac arteries which are frequently tortuous. Precise positioning of the graft could be impaired because the pusher wire is not attached to the graft. This poses the potential for mispositioning of the graft during the withdrawal of the sheath. Hemorrhage could also be a major problem with this method of introduction. The introducer sheath is carried into position on the outside of a dilator, which must be removed before the graft can be inserted, leaving the sheath as a conduit from the artery to the outside of the body. The need to introduce the graft complicates the use of hemostatic seals on the sheath. Only one of these grafts carried barbs. The other model showed a tendency to migrate. There is a possibility that the sheathed wall of the barbed device could be breached by the barbs during transfer of the graft to the point of repair because the graft is pushed though the entire length of the catheter with the springs expanded against the inner wall of the catheter. Also, the wide mesh of the material used may not form a barrier to blood leaks, so that the aneurysm could be exposed to arterial pressure.

Endovascular repair of abdominal aortic aneurysm avoids much of the morbidity and mortality associated with conventional surgery. Most patients with abdominal aortic aneurysm lack a segment of non-dilated aorta suitable for attachment of the down stream (caudal) end of a straight (single-lumen) endovascular graft. In these patients a more secure outflow is provided by attaching the two caudal ends of a bifurcated graft to the iliac arteries.

The caudal ends of bifurcated grafts cannot extend to the sites of arterial access in the groin without impairing internal iliac arterial flow, which is an important source of spinal and colonic perfusion after aortic aneurysm repair. Therefore, direct control of the caudal ends of bifurcated grafts is not possible, resulting in a tendency to kinking, twisting and displacement, all of which have complicated previous attempts to apply this approach. The devices and techniques described below provide a means of accurate, hemostatic and permanent insertion of a bifurcated graft, with provision for the prevention of correction of these potential complications.

SUMMARY OF THE INVENTION

The present invention provides a transluminal graft prosthesis that can be safely and precisely positioned.

An object of the present invention is to provide a prosthesis for the safe repair of aneurysms without the risks associated with invasive surgical repair.

It is another object of the invention to provide a coupling between a plurality of spring expanding assemblies that provides a relatively flexible prosthesis during insertion, a relatively rigid prosthesis after attachment, and also maintains the alignment of the springs when the prosthesis is compressed by an extrusion device applied to one end.

The present invention provides a device for transluminal grafting of a prosthesis in a lumen, comprising:
a tubular introducer sheath having a longitudinal bore; a prosthesis comprising a tubular graft having a longitudinal bore and disposed in the longitudinal bore of the tubular introducer sheath, the graft being expandable radially to substantially conform to the interior wall of a lumen; a spring expanding assembly permanently attached to the tubular graft to expand the graft so that it substantially conforms to the interior wall of a lumen when the graft is removed from the introducer sheath; an anchoring means for permanently attaching the graft to an interior wall of a lumen; a tubular carrier means having a longitudinal bore and disposed in the longitudinal bore of the tubular graft, the tubular carrier means provided with a plurality of apertures; a central control means for maintaining the axial position of the prosthesis during removal of the introducer sheath, the central control means disposed in the longitudinal bore of the tubular carrier means; and mooring loops engaging the prosthesis and passing through the apertures in the tubular carrier means to engage the central control means.

The present invention also provides a method for engrafting a prosthesis in a lumen comprising the steps of a) providing an access to the lumen; b) providing a device for engrafting the prosthesis comprising: a tubular introducer sheath having a longitudinal bore; a tubular graft having a longitudinal bore and disposed in the longitudinal bore of the tubular introducer sheath, the graft being expandable radially to substantially conform to the interior wall of a lumen; a spring expanding assembly permanently attached to the tubular graft to expand the graft so that the graft substantially conforms to the interior wall of a lumen when the graft is removed from the introducer sheath; an anchoring means for permanently attaching the graft to an interior wall of a lumen; a tubular carrier means having a longitudinal bore and disposed in the longitudinal bore of the tubular graft, the tubular carrier means provided with a plurality of apertures; a central control means for maintaining the axial position of the prosthesis during removal of the introducer sheath, the central control means disposed in the longitudinal bore of the tubular carrier means; mooring loops engaging the prosthesis and passing through the apertures in the tubular carrier means to engage the central control means; c) inserting the device and urging the device into a lumen to a desired location within the lumen; d) withdrawing the tubular introducer sheath to expose the graft; e) disengaging the central control means from the mooring loops; and f) removing the tubular introducer sheath, carrier means, and central control means.

The present invention provides an occlusive umbrella comprising: a spring expanding assembly having a proximal and a distal end; barbs attached to the proximal end of the spring means; a tubular graft having a longitudinal bore and having a proximal end and a distal end, the tubular graft open at the proximal end and closed at the distal end, the graft attached to the spring; a dilator having a distal end and a proximal end, the proximal end of the dilator attached to the distal end of the tubular graft; a first tubular catheter having a proximal end, a distal end, and a longitudinal bore, the first tubular catheter inserted into the longitudinal bore of the graft and attached to the proximal end of the dilator; a second tubular catheter having a proximal end, a distal end, and a longitudinal bore, the distal end of the second catheter communicating with the proximal end of the first catheter; a flexible rod having a proximal end and a distal end, the distal end of the flexible rod inserted into the longitudinal opening of the first catheter and the longitudinal opening of the second catheter, the distal end of the flexible rod contacting the dilator head.

The present invention provides a flexible spring alignment and compression resistance assembly comprising: a first and second spring expanding assembly each having a plurality of apertures; a plurality of retaining shafts each having a first end and a second end, the shafts having a diameter equal to or smaller than the apertures of the first and second spring expanding assemblies, the first end of each of the retaining shafts slidably inserted into one of the apertures of the first spring expanding assembly and the second end of each of the retaining shafts slidably inserted into one of the apertures of the second spring expanding assembly, a first protrusion attached to each of said first ends and a second protrusion attached to each of said second ends, the protrusions larger than the apertures of the first and the second spring expanding assemblies to prevent the protrusions from passing through the apertures.

The present invention also provides a flexible spring alignment and compression resistance assembly comprising: a first spring expanding assembly having a plurality of apertures; a second spring expanding assembly; a plurality of retaining shafts each having a first end and a second end, the shafts having a diameter equal to or smaller than the apertures of the first spring expanding assembly, the first end of each of the retaining shafts slidably inserted into one of the apertures of the first spring expanding assembly and the second end of each of the retaining shafts attached to the second spring expanding assembly, a protrusion attached to each of said first ends, the protrusions larger than the apertures in the first spring expanding assembly to prevent the protrusions from passing through the apertures.

The foregoing problems are solved and a technical advance is achieved in an illustrative prosthesis for repairing an aneurysm. The prosthesis comprises a bifurcated endovascular graft having a main body and first and second limbs extending therefrom. The main body includes a main bore extending longitudinally therein and having a cranial orifice. The first limb includes a first bore extending longitudinally therein, communicating with the main bore, and having a first caudal orifice. The second limb includes a second bore extending longitudinally therein, communicating with the main bore and having a second caudal orifice. The prosthesis also comprises a first imageable marker extending longitudinally along the first limb and a second imageable marker extending longitudinally along the first limb and spaced at least a predetermined distance away from the first marker.

The invention also comprises an illustrative prosthesis delivery system for percutaneously inserting the prosthesis in an aneurysm. The delivery system comprises a tubular introducer sheath having a sheath bore extending longitudinally therein and a central carrier coaxially positionable within the sheath bore of the sheath. The central carrier includes a head region having a dimension approximating said sheath bore, a shaft region having a dimension approximating the sheath bore, and a stem region positioned between the head and shaft regions and having a dimension smaller than the sheath bore for positioning the prosthesis therearound and in the sheath bore.

The present invention also includes an illustrative method of inserting a bifurcated prosthesis in an aneurysm utilizing the prosthesis delivery system. The method comprises the steps of percutaneously obtaining cross access with a first guide between femoral arteries positioned caudal to the aneurysm; percutaneously obtaining access to a lumen of the aneurysm with the second guide; and positioning the prosthesis in the aneurysm and one limb thereof in one of the femoral arteries with the prosthesis delivery system and the second guide. The method also comprises the steps of positioning another limb of the prosthesis in the other of the femoral arteries with the first guide and releasing the prosthesis from the delivery system when the prosthesis is positioned in the aneurysm.

The invention is described in greater detail below based on a few selected embodiments. Those skilled in the art will appreciate that the prosthesis according to the invention can be applied in various modifications.

The foregoing problems are also solved and another technical advance is achieved by an illustrative transluminal arrangement for positioning a prosthesis assembly in a particular bifurcated lumen. The bifurcated lumen includes, for example, the main lumen of the aorta and the branch lumens of the common iliac arteries. An aneurysm is commonly found in the aorta just proximal the branching of the common iliac arteries. A prosthesis assembly for positioning in the aneurysm of the bifurcated lumen includes a bifurcated endovascular graft having a main body and first and second limbs extending therefrom. The assembly also includes main and branch limb spring assemblies each having a compressed state. The main bore spring assembly radially expands to substantially conform the main body of the graft to the interior wall of the aortal lumen. The ipsilateral and contralateral limb spring assemblies radially expand to conform the limbs of the graft to the interior walls of the branch lumens of the ipsilateral and contralateral iliac arteries. The transluminal arrangement comprises containers such as sheaths for containing each of the spring assemblies in a compressed state and a retainer assembly positioned in the main and ipsilateral bores of the graft for retaining the prosthesis assembly at the aneurysm in the bifurcated lumen while the main outer sleeve is withdrawn from the prosthesis assembly, thereby releasing the main spring assembly from its compressed state. Branch limb retainer means attached to the ipsilateral and contralateral spring assemblies retain these spring assemblies in respective container sheaths.

The main container includes an outer sheath with a longitudinal bore wherein the prosthesis assembly is positioned. The ipsilateral and contralateral containers each include a sheath with a longitudinal bore wherein the ipsilateral and contralateral spring assemblies are positioned and contained in their compressed state.

The main retainer assembly of the transluminal arrangement comprises an elongated member having a dilator head at the distal end thereof, a main attachment assembly for temporarily attaching the main spring assembly to the elongated member and a branch limb attachment assembly for temporarily attaching the branch limb spring assembly to the elongated member. An inner catheter is positioned through the elongated member for releasing at least one of the main and ipsilateral attachment assemblies either during or after removal of the main and first sheaths. A control limb delivery catheter forms a second release assembly, which is temporarily attached to the contralateral spring assembly with an attachment suture extending therethrough for releasing the contralateral spring assembly when positioned in the contralateral common iliac artery.

The main and ipsilateral attachment assemblies each comprise attachment sutures for temporarily pulling the main and ipsilateral spring assemblies inwardly to their compressed state when the prosthesis assembly is positioned within the main sheath.

The transluminal arrangement also includes a method of positioning the prosthesis assembly at the aneurysm in the bifurcated lumen. The method includes providing cross access to the branch lumens and inserting a cross femoral wire guide between the branch access sites. The transluminal arrangement is positioned in the bifurcated lumen via the ipsilateral access site. The outer sheath is withdrawn from the prosthesis assembly and the contralateral limb is positioned with the aid of the cross femoral guide pulling the control limb delivery catheter of the transluminal arrangement. The attachment sutures are released from the prosthesis assembly when positioned at the aneurysm in the bifurcated lumen allowing the main spring assembly to radially expand and conform the graft to the aorta. The branch limb containers of the transluminal arrangement are also withdrawn from the branch spring assemblies which then radially expand the ipsilateral and contralateral limbs of the graft to the common iliac arteries so as to advantageously prevent retrograde flow of blood back to the aneurysm. Similarly, the main spring assembly conforms the cranial orifice of the main body of the graft to the wall of the aorta preventing antegrade flow of blood into the aneurysm.

BRIEF DESCRIPTION OF THE DRAWINGS

FIG. 7 is a side view of a flexible spring alignment and compression resistance assembly;

FIG. 8 shows the elbow and retaining bar of the flexible spring alignment and compression resistance assembly of FIG. 7;

FIG. 9-A is a longitudinal cross-sectional view of two compressed spring expanding assemblies connected by the flexible spring alignment and compression resistance assembly of FIG. 7;

FIG. 9-B is a longitudinal cross-sectional view of two uncompressed spring expanding assemblies connected by the flexible spring alignment and compression resistance assembly of FIG. 7.

FIG. 10 is a side-view of a flexible spring alignment and compression resistance assembly and shows the retaining bar rigidly attached to one of the spring expanding assemblies;

FIG. 11 is a longitudinal cross-sectional view of a tubular carrier of the instant invention shown with a dilator head at the distal (upstream) end;

FIG. 12 is a longitudinal cross-sectional view of a "muzzle loading" apparatus of the instant invention;

FIG. 13 is a longitudinal cross-sectional view of the proximal (downstream) end of the introducer sheath;

FIGS. 26 and 27 depict a carrier of the present invention;

FIG. 28 depicts tubular extensions sutured to a graft of the present invention;

FIG. 29 depicts an alternative mechanism for attaching the tubular extensions to a graft of the present invention;

FIG. 40 depicts a contralateral limb straightening device;

FIG. 44 depicts a partially sectioned side view of ipsilateral limb spring assembly of the prosthesis assembly and stent boot of the transluminal arrangement of FIG. 43;

FIG. 45 depicts a partially sectioned side view of contralateral spring assembly of the prosthesis assembly and control limb delivery catheter of FIG. 43;

DETAILED DESCRIPTION

Figure 1:
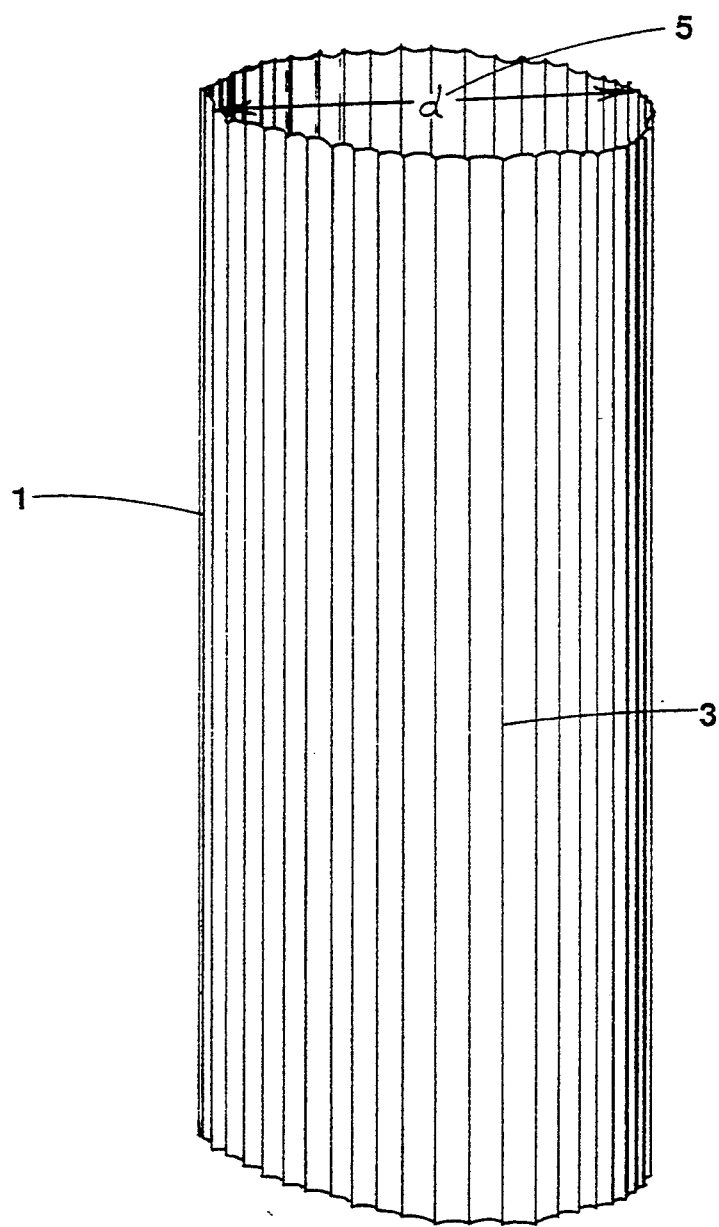
FIG. 1 is a side view of a tubular graft of the instant invention.

The graft 1 shown in FIG. 1 is in the form of an elongated cylindrical tube defining a longitudinal bore that is multiply crimped 3, or folded over to facilitate the compression and expansion of the graft as the diameter 5 of the graft decreases and increases. Transverse elasticity may also be achieved or enhanced through inherent properties of either the weave or constituent fibers used to construct the graft 1. The graft 1 is preferably constructed from a material such as woven multi-filament polyester (such as Dacron TM), which is known to be sufficiently biologically inert, non-biodegradable, and durable to permit safe insertion inside the human body. Any material with such qualities may be used, however. Polyester is also known to excite fibrous ingrowth which will secure the graft 1 to the wall of the lumen within a few months of its insertion.

The typical graft 1 is of fixed length and relatively inelastic along its longitudinal axis. A variable length graft may also be used and could be constructed by either having two pieces of graft, one inserted within the other in a telescopic arrangement, capable of being manipulated within the body, or having one continuous piece of material that is folded back on itself. A spring within this area of the graft ensures apposition of the various layers at this level; the outer layers having a slightly smaller maximum diameter to provide a buttress against which the spring can expand in the absence of a secure arterial wall. Variability of length may also be achieved by providing elasticity along the longitudinal axis of the graft as a property of graft material or by having one or more elastic sections of such material within the main body of the graft.

Figure 2:
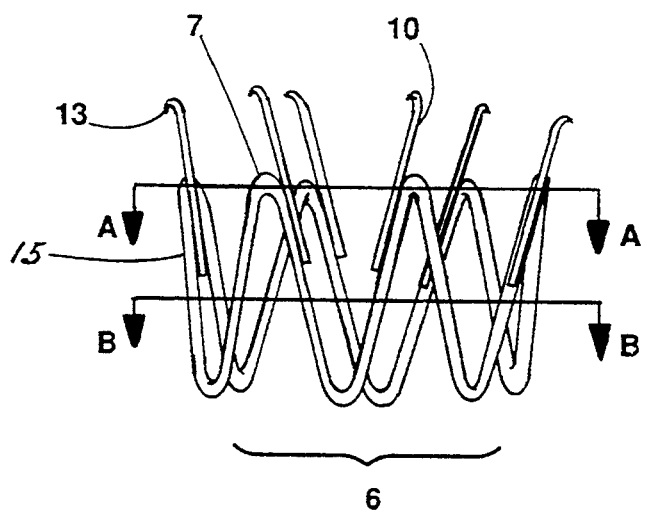
FIG. 2 is a side view of a spring expanding assembly of the instant invention.
Figure 3:
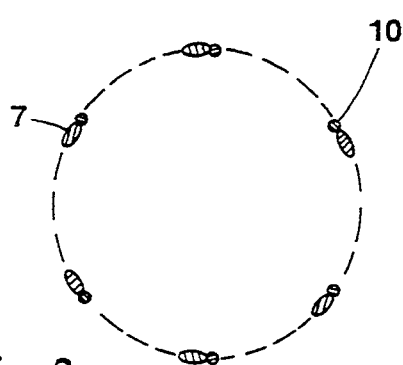
FIG. 3 is a top cross-sectional view of a spring expanding assembly shown in FIG. 2 taken along A—A.
Figure 4:
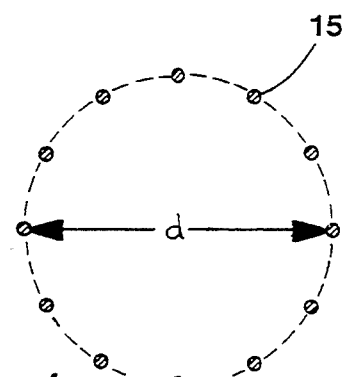
FIG. 4 is a top cross-sectional view of a spring expanding assembly shown in FIG. 2 taken along B—B.
Figures 5A, 5B, 5C:
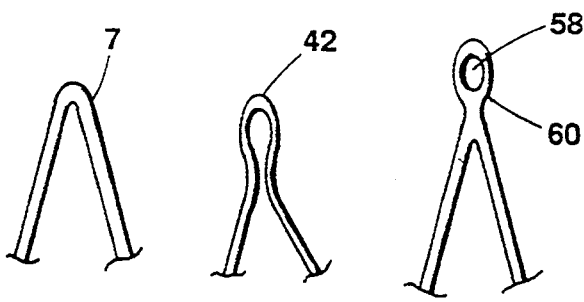
FIG. 5 is a side view of alternative elbows of the spring expanding assembly of the instant invention.
Figure 6:
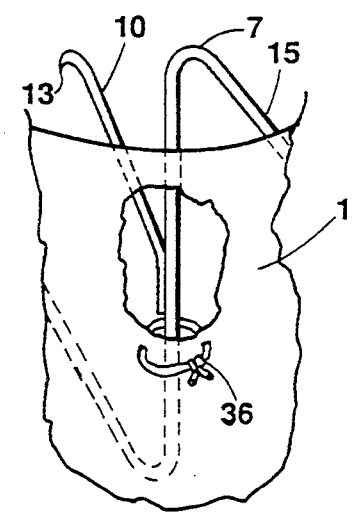
FIG. 6 shows a spring expanding assembly (with a barb attached) sutured to the graft.

The spring assembly 6 of FIG. 2 includes arms 15 which are bent to form elbows 7. Surgical barbs 10 having sharp tips 13 are attached to the arms 15 and protrude from the elbows 7. FIG. 3 is a top cross-sectional view of the spring assembly 6 of FIG. 2 taken along A—A showing six elbows 7 and associated barbs 10. FIG. 4 is a top cross-sectional view of the spring assembly 6 taken along B—B showing twelve arms 15 which extend from the six elbows 7 shown in FIGS. 2 and 3. A spring assembly 6 is typically formed from a continuous piece of fine gauge stainless steel spring wire that, if opened out, would appear in the shape of a zig-zag with multiple elbows 7. FIG. 5 shows that these elbows 7 may be simple arches 7, recurved arches 42, or apertured 60. The advantage of simple arches 7 is that the spring assembly 6 expands the longitudinal aperture of the graft 1 more evenly. The advantage of the recurved arches 42 is that they collapse more readily and are more durable. The apertured elbows 60 are used in the flexible spring alignment and compression resistance assembly. The two ends of the piece of bent wire are permanently attached end-to-end so as to form a circular structure, e.g., FIGS. 2, 3 and 4. FIG. 6 shows a portion of the spring assembly 6 with a barb 10 attached to an arm 15 of the spring assembly 6. The spring assembly 6 is sutured to the graft 1 with a non-biodegradable thread 36. The spring assembly 6 may also be constructed out of other inert metals such as titanium, or a plastic. When expanded, the spring assembly 6 is circular in shape when viewed from above, and may have a diameter, when in a relaxed state, equal to approximately twice the diameter of a lumen into which the graft 1 is to be inserted. The spring assembly 6 is typically attached to the inside of the cylindrical graft 1 at the distal (upstream) end or both ends of the graft 1 by sutures 36 of non-biodegradable material. The sutures 36 attach to the spring assembly 6 in such a way that the majority of the spring assembly 6 is covered by the graft material 1. Other embodiments may incorporate spring assemblies 6 being attached to the outside of the tubular graft 1 which would present a smoother surface to the flowing blood but has the drawback that the graft 1 would be in less intimate contact with the wall of the lumen.

The spring assembly 6 on the distal (upstream) end of the graft 1 has small surgical barbs 10 firmly attached to the spring assembly 6. The spring assembly 6 at the proximal (downstream) end of the graft may also be provided with barbs. The attachment of the barbs 10 to the graft 1 or spring assembly 6 must be permanent and can be either welded, brazed, or coupled in a fashion that is both biologically acceptable, and yet strong enough to withstand long-term stress. These barbs 10 spread radially outward from the longitudinal axis of the graft 1, such that when the spring assembly 6 opens inside the lumen, the barb tips 13 will come into contact with and engage the wall of the blood vessel to be repaired. The barb tips 13 will become imbedded in the wall through both the driving action of the spring assembly 6 and the pressure created by the flow of blood through the graft 1. The barb tips 13 are sharp and may be curved slightly downward toward the graft 1 to provide a more secure anchor in the direction of blood flow. The barbs 10 are positioned so that they are further upstream than the elbows 7 of the distal (upstream) spring assembly 12, and are of such a size that the wall of the blood vessel is not punctured or pierced when the barb tips 13 are firmly embedded therein. Attaching the barbs 10 to the spring assembly 6 via shafts bonded to the spring assembly 6 at the middle of one of the two arms 15 extending from an elbow 7 of the spring assembly 6 permits the barb tip 13 to slightly retract or rotate when compressed for loading into the introducer sheath 4 (as best seen in FIG. 6).

Though the spring assembly 6 is typically sutured only to the ends of the graft 1, several such spring assemblies 6 may also be connected to one another for added strength. This is necessary in embodiments of the prosthesis that require the graft to resist compression during removal from the introducer 4. Some flexibility is retained by connecting the spring assemblies 6 to each other in a way that permits separation (but not overlapping or misalignment) of adjacent spring elbows 60. FIG. 7 illustrates such a flexible spring alignment and compression resistance assembly 49 and shows a first spring arm 50 and a second spring arm 52 connected via a retaining bar 54. The retaining bar 54 is constructed of fine gauge wire with a protrusion 56 at each end. FIG. 8 shows a modified elbow 60 and includes an aperture 58 provided to receive the retaining bar 54. The retaining bar 54 slides through apertures 58 provided in the modified elbows 60 of adjacent arms 50 and 52. The rigidity of the retaining bar 54 prevents overlapping during compressive loading of the prosthesis, while the protrusions 56 prevent disassociation of the joints during flexion of the graft which might otherwise disrupt the chain of springs 50 and 52. The shaft 62 of the retaining bar 54 has a diameter slightly smaller than aperture 58 and the protrusion 56 has a diameter slightly larger than the aperture 58. The slidably mounted retaining bars 54 allow arms 52 and 54 to separate but prevent arms 52 and 54 from sliding over one another.

It is desirable that the joint between the spring assemblies 6 be flexible during the introduction and relatively rigid once the graft has been implanted. As shown in FIGS. 9-A and 9-B, the joint is more flexible when the spring assemblies 64 and 66 are compressed (i.e., during insertion) and relatively rigid when the spring assemblies 64 and 66 are in an uncompressed state (i.e., after implantation). FIGS. 9-A and 9-B show a first spring assembly 64 connected to a second spring assembly 66 by a flexible spring alignment and compression resistance assembly 49. FIG. 9-A shows the spring assemblies 64 and 66 in a compressed state and FIG. 9-B shows the spring assemblies 64 and 66 in an uncompressed state. Angle $\alpha$ represents the maximum angle between spring assemblies 64 and 66 when the springs are in a compressed state and angle $\beta$ represents the maximum angle between spring assemblies 64 and 66 when the springs are in an uncompressed state. Thus, the angle between spring assemblies 64 and 66 decreases with an increase in the transverse diameter of spring assemblies 64 and 66. The angle of flexion will be largest when spring expanding assemblies 64 and 66 are in a compressed state (diameter $d_1$) and the angle of flexion will be smallest when spring expanding assemblies 64 and 66 are in an uncompressed state (diameter $d_2$). Thus, because $\alpha$ is larger than $\beta$, the prosthesis becomes more rigid as its diameter increases. During insertion, the graft 1 is confined within the introducer sheath 4 and remains both narrow and flexible. After removal from the sheath 4 the graft 1 expands becoming more rigid.

The retaining bar 54 may also be non-slidably attached at one (but not both) of its ends to one of the spring expanding assemblies 51 as shown in FIG. 10.

FIG. 11 shows a tubular carrier 21 which has a dilator head 22 mounted at the distal (upstream) end. The dilator head 22 may have a distal (upstream) conical portion 75 and a proximal (downstream) cylindrical portion 74. The dilator head 22 may have a soft tipped guide-wire 68 protruding from its distal (upstream) end. The cylindrical portion 74 of the dilator 22 has a diameter d equal to the internal diameter of the introducer sheath 4.

FIG. 12 shows the assembled "muzzle loading" apparatus and includes a tubular carrier 21 with a dilator head 22 at the distal (upstream) end; dilator head lip 27; introducer sheath 4; graft 1 which is slid onto the tubular carrier 21; distal (upstream) spring assembly 12; proximal (downstream) spring assembly 31; central control means 26 which is inserted into the tubular carrier 21; distal (upstream) end 8 of the graft 1; proximal (downstream) 9 end of the graft 1; and non-biodegradable sutures 36 that permanently attach the spring assemblies 12 and 31 to the graft 1. If the outer diameter of the tubular carrier 21 is equal to the internal diameter of the introducer sheath 4, leakage of blood between the two is minimal. Alternatively, the introducer sheath 4 may be closed at its proximal (downstream) end by a small rubber seal 70 as shown in FIG. 13 which has an aperture 72 for receiving the carrier 21.

"Muzzle loading" involves inserting the graft 1, already mounted on the tubular carrier 21, into the distal (upstream) end of the introducer sheath 4 before insertion of the introducer sheath 4 into the lumen. "Breech loading" involves inserting the graft 1 into the introducer sheath 4 from the proximal (downstream) end of the sheath 4, after the introducer sheath 4 has been inserted into the patient and is in position.

"Muzzle loading" has two main advantages that make it the preferred means of operation. The first advantage of "muzzle loading" over "breech loading" is the lower probability of hemorrhage. In the "breech loading" technique, the dilator 22 must be removed before the graft 1 can be inserted, leaving the introducer sheath 4 as a large conduit between the arterial circulation and the outside of the body. Any effective seal in the introducer sheath 4 will obstruct insertion of the graft 1 unless this is carried within a second sheath (with the consequent increase in size). The only other way to control the hemorrhage is to clamp the introducer sheath 4 on the outside, however, clamping is unlikely to be totally occlusive and may damage the introducer sheath 4. Moreover, the clamp must be removed to allow passage of the graft 1 which produces another period of rapid hemorrhage.

The second advantage of "muzzle loading" over "breech loading" is that if a single sheath 4 is to be used in the "breech loading" technique, the graft 1 must be placed within the introducer 4 at the time of operation. This can be a tricky procedure, especially when the outer end of the introducer sheath 4 is issuing a continual stream of blood.

Figure 14:
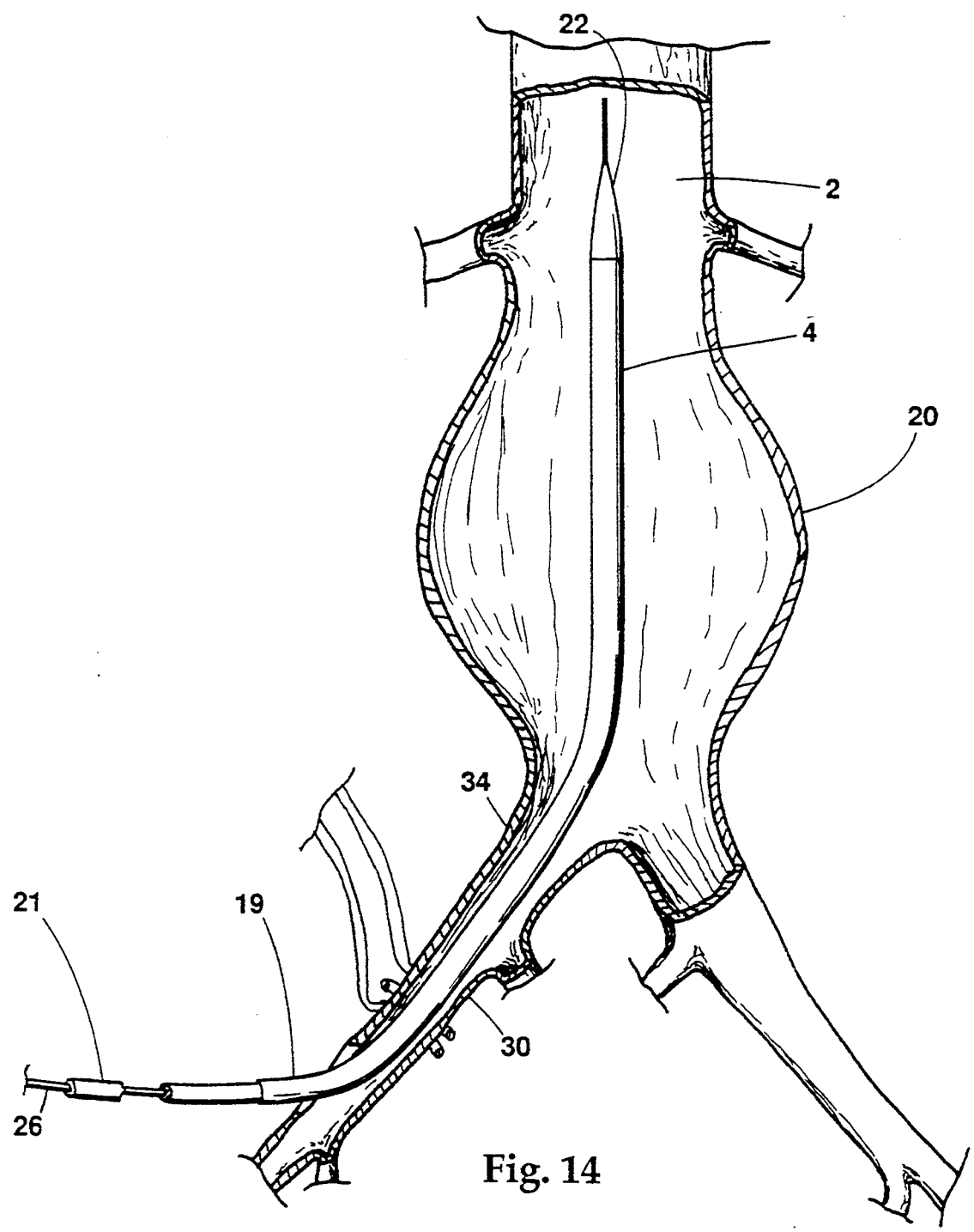
FIG. 14 is a longitudinal cross-sectional view of the aorta and iliac arteries and shows a dilator head, introducer sheath, tubular carrier, arteriotomy, and central control means.
Figure 15:
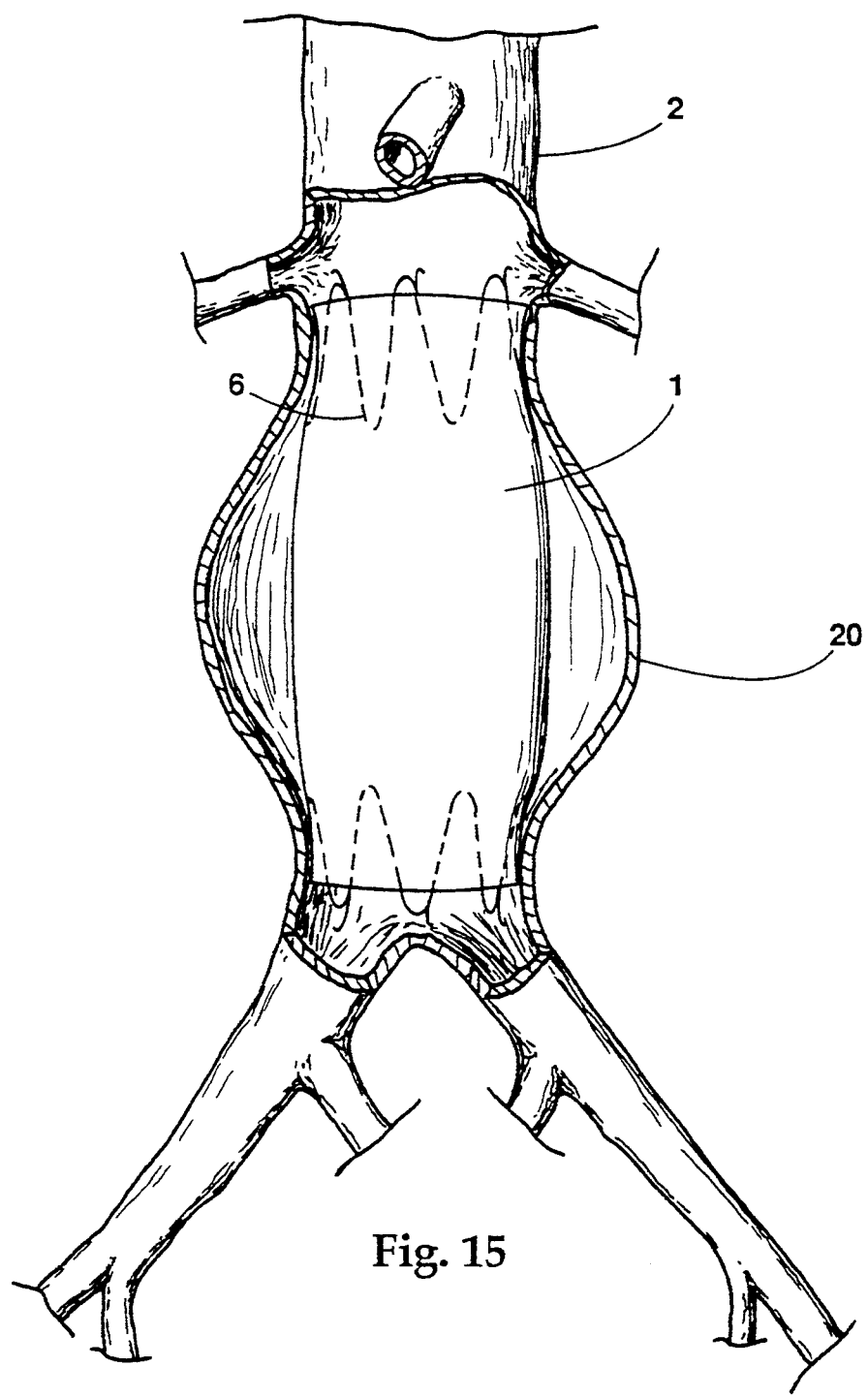
FIG. 15 is a longitudinal cross-sectional view of the aorta and iliac arteries and shows a graft implanted in the aorta on either side of an aneurysm.

FIG. 14 shows the common femoral artery 30; proximal (downstream) end 19 of the introducer sheath 4; tubular carrier 21; iliac artery 34; aorta 2; aortic aneurism 20; dilator head 22; and central control means 26. FIG. 15 shows the graft 1 implanted in the aorta 2 at the site of the aortic aneurysm 20.

In the "muzzle loading" technique the graft 1 is inserted into the distal (upstream) end of the introducer sheath 4. The introducer sheath 4 is thin walled, smooth, flexible, sterilizable, non-toxic, and is tubular in form. The tubular carrier 21 fits inside the introducer sheath 4. A close match between the sizes of the sheath 4 and carrier 21 helps to eliminate any buckling of the tubular carrier 21 within the sheath 4 while simultaneously limiting the seepage of blood between the carrier 21 and the sheath 4. The tubular carrier 21 has a dilator 22 attached to the distal (upstream) end which has a conical tip 75 to facilitate the atraumatic passage of the apparatus from the groin into the upper end of the aneurysm. The dilator 22 is also provided with a cylindrical portion 74 on its proximal (downstream) end which mates with the introducer sheath 4.

The introducer sheath 4 fits over the cylindrical portion 74 of the dilator head 22. A tiny lip 27 at the junction between cylindrical portion 74 and conical portion 75 of the dilator head 22 overlaps the end of the introducer sheath 4 so that no edges are presented to the arterial lumen (or the thrombus that lines the aneurysm) during introduction of the apparatus. This reduces the trauma to vessels and minimizes the chance of dislodging a piece of thrombus that could embolize into the kidneys or lower limbs.

The central control means 26 may take the form of a catheter which extends the entire length of the carrier to the tip of the dilator head 22 so that its lumen can be used for the injection of angiographic dye or as a means of threading the apparatus over a previously placed guide wire. Alternatively, the central control means 26 may pass all the way through the dilator head 22 and slide back and forth within the carrier 4 so that it may function as a guide wire itself. This has been found to be useful in the technique of percutaneous insertion.

In the "breech loading" device, the introducer sheath 4 is a tubular structure having a uniform-diameter and is made of the same material as the "muzzle loading" introducer sheath 4. With this design, the tubular carrier 21 does not have a dilator 22 because the introducer sheath 4 can be carried into position around a standard dilator, which would then be removed before insertion of the tubular carrier 21 with the graft 1.

Figure 16:
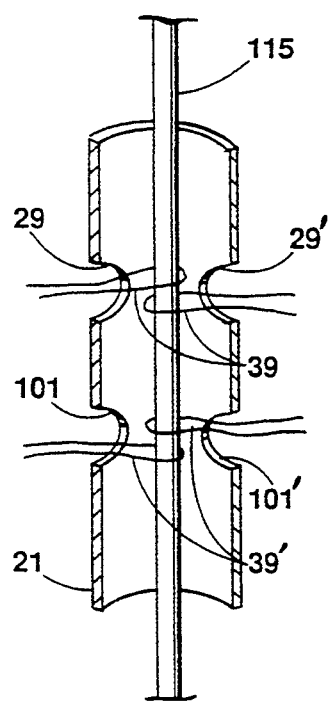
FIGS. 16 and 17 are longitudinal cross-sectional views of an apertured tubular carrier showing mooring loops and central control means.

FIG. 16 shows the tubular carrier 21; mooring loops 39; central control wire 15; and apertures 29, 29', 101, and 101' in the wall of tubular carrier 21.

Figure 17:
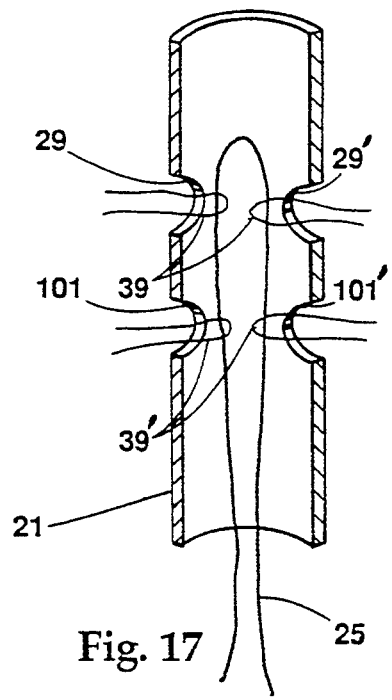

FIG. 17 shows the tubular carrier 21; mooring loops 39 and 39'; apertures 29, 29', 101 and 101' in the wall of the tubular carrier 21; and central control thread 25.

All "muzzle loading" (and some "breech loading") devices use a central control means 26 that runs up the center of the tubular carrier 21, to which the graft 6 may be moored, and which is used for maintaining the axial position of the graft 1 during removal of the introducer sheath 4. This central control means 26 can take one of several forms, including a flexible shaft 115 (such as a stainless steel wire or a narrow catheter) (as shown in FIG. 16) or a simple thread 25 (as shown in FIG. 17) that passes up the center of the tubular carrier 21, through the mooring loops 39 and 39', and then doubles back through the center of the tubular carrier 21 to its point of origin outside the patient. In the absence of mooring loops 39 and 39', this thread 25 can exit an aperture (29, 29', 101 and 101'), pass through an elbow 7 of the spring assembly 6, traverse the apertures to the opposite elbow 7 of the spring assembly 6 (which it also encircles), pass back into the lumen of the carrier 21 through an aperture (29, 29', 101, and 101') and thereby return to the proximal end of the catheter 21. Release of the mooring loops 39 and 39' is accomplished by withdrawing the central control shaft 115 from the tubular carrier 21 or by releasing one end of the central control thread 25, which is then removed from the tubular carrier 21. If each end of the graft 1 is desired to be controlled and positioned independently of the other, the central control shaft 115 can be partially withdrawn to a point in between the two sets of mooring loops 39 and 39'. If the central control means 26 is a central control thread 25 (instead of a flexible shaft 115), multiple threads 25 can be used, one for each set of mooring loops 39 and 39'.

Because it has no dilator head, the carrier of the "breech loading" device need not traverse the graft 1 to the distal (upstream) end of the introducer sheath 4. Instead, it can end at the graft 1 which would be pushed rather than pulled from the sheath 4. No attachment to the graft 1 would then be needed, but the graft 1 would have to be more rigid and placement would be less precisely controlled.

The "muzzle loading" method will now be described. To assemble the apparatus prior to insertion, the central control means 26 is inserted through the entire length of the tubular carrier 21, which, in turn, is inserted through the entire length of the introducer sheath 4. With the end of the tubular carrier 21 and central control means 26 protruding past the top of the introducer sheath 4, the graft 1 is slid over the dilator head 22 and down the outside of the tubular carrier 21 until positioned directly below the tapered dilator head 22 of the tubular carrier 21. As shown in FIG. 16, the distal (upstream) end of the graft 1 is then moored around the central control means 26 with a mooring loop 39 that engages the spring assembly 6, or is sutured to the graft 1. The mooring loop 39 enters the tubular carrier 21 via the aperture 29 and 29' and forms a mooring loop 39 which engages the central control means 26 so that the mooring loops 39 cannot exit the carrier 21 while the control means 26 occupies the longitudinal opening of the tubular carrier 21. These mooring loops 39 will remain attached to the graft 1 or springs 6 after placement of the graft 1. The mooring loops 39 are preferably made of a monofilament material of low thrombogenicity that in some applications may be biodegradable. When the central control means 26 is withdrawn, mooring loops 39 are free to exit the tubular carrier 21. The proximal (downstream) end of the graft 1 can also be secured in the same manner through a second set of mooring loops 39' passing through a second set of apertures 101 and 101' in the tubular carrier 21, thereby facilitating independent positioning of the two ends of the graft 1. Once the graft 1 is compressed, the introducer sheath 4 is slid over the tubular carrier 21 and the edge of the introducer sheath 4 is fitted snugly against the lip 27 of the dilator head 22. The barbs 10 on the distal (upstream) spring assembly 12 are completely covered by the introducer sheath 4. The apparatus is now ready for insertion.

Figure 18:
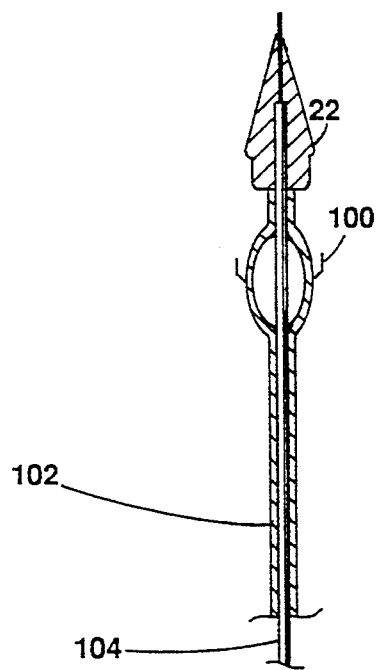
FIG. 18 is a longitudinal cross-sectional view of an alternative means of graft attachment.

FIG. 18 is a longitudinal cross-sectional view of an alternative embodiment of the carrier catheter that does not employ a central control means and shows cantilevered hooks 100, outer carrier 102, inner catheter 104, and dilator head 22. In this embodiment, a pair of concentric catheters is bonded at the distal (upstream) end such that when the inner catheter 104 is pulled in the proximal (downstream) direction from outside the body, the outer catheter 102 bulges out. The graft 1 is held in position on the outer catheter 102 by means of cantilevered hooks 100 attached to the outer surface of the outer catheter 102. These hooks 100 engage the spring assembly 6 of the graft 1 during insertion and prevent the graft 1 from changing its axial position while the introducer sheath 4 is withdrawn. The graft 1 is released from the hooks 100 when the outer catheter 102 is withdrawn.

These methods of securing the graft to the carrier for selective release are required because the outward expansion of the graft against the sheath generates considerable friction that must be overcome in order to extrude the graft. Without such a mechanism, the graft would move with the sheath and would be imprecisely extruded. In order to minimize the forces involved in extrusion, the sheath is constructed of a material (such as Teflon ™) which has a low friction surface or is coated with a lubricous material (such as hydragel polymer).

The insertion procedure may be a surgical procedure or may be accomplished percutaneously using a guide wire. In the surgical approach, for example, the femoral artery 30 is exposed through a short groin incision. Heparin is administered intravenously, hemostatic clamps or bands are applied, and the femoral artery 30 is opened. The complete apparatus is inserted into the open femoral artery 30, and is pushed through the femoral 30 and iliac 34 arteries into the aorta 2. The graft 1 is positioned so as to cover the entire length of the aortic aneurysm 20. Positioning is confirmed through fluoroscopy and angiography. Once the positioning has been confirmed, the introducer sheath 4 is pulled back exposing the distal (upstream) barbed spring assembly 12 and part of the length of the graft 1. The springs expand driving the barb tips 13 into the wall of the aorta 2. Once the entire graft 1 is out of the introducer sheath 4 the central control means 26 is withdrawn. As the central control means 26 is withdrawn past the point where the graft 1 is moored to the central control means 26 via the mooring loops 39, the mooring loops 39 will pass over the end of the central control means 26 and be free to pass through the apertures 29 and 29' in the tubular carrier 21. Blood flow in the aorta 2 aids in opening up the multiply crimped middle portion of the graft 1. Placement is performed in two stages. First, the introducer sheath 4 is withdrawn to expose the distal (upstream) 8 half of the graft 1 which expands and attaches to the wall of the aorta 2. The central control means 26 is then withdrawn to a point between the holes 29 and 29' and 101 and 101' in the tubular carrier 21, leaving only the proximal (downstream) 9 end of the graft 1 attached to the carrier 21. The proximal (downstream) 9 end of the graft 1 can then be positioned independently of the distal (upstream) 8 end of the graft 1. The introducer sheath 4 is then withdrawn over the proximal (downstream) spring assembly 31. When the proximal (downstream) 9 end of the graft 1 is exposed it also expands under the action of the spring assembly 31, driving the barbs 10 (when present) into the wall of the aorta 2. The central control means 26 can then be withdrawn past the point where the central control means 26 engages the second set of mooring loops 39', thereby releasing the graft 1 completely. After the proximal (downstream) spring assembly 31 has been released, the tubular carrier 21, central control means 26, and introducer sheath 4 are removed from the patient's body. The femoral artery 30 is then repaired and the wound closed.

Figure 19:
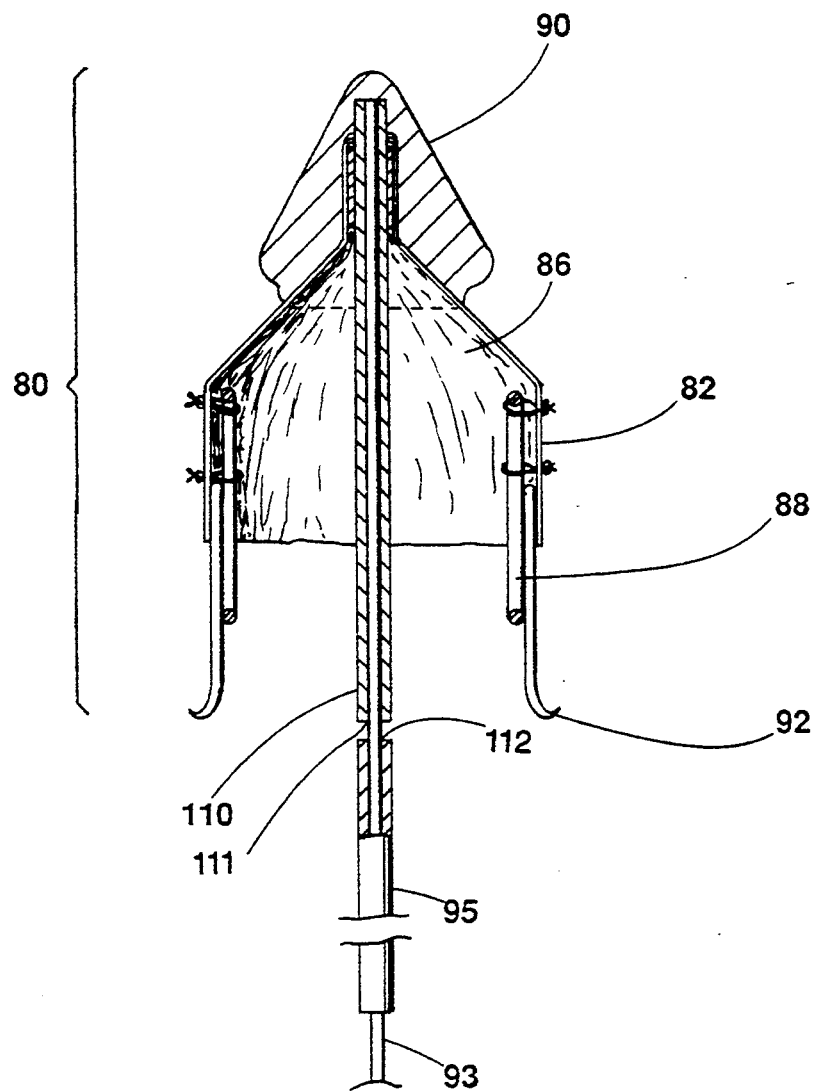
FIG. 19 is a longitudinal cross-sectional view of an occlusive umbrella.

Aortic aneurysms frequently encompass the entire distal aorta. In these cases, there is no normal aorta between the aneurysm and the iliac arteries. In order to provide a secure arterial wall for the attachment of the proximal (downstream) end of the graft, the graft may be placed from the infrarenal aorta, above the aneurysm, into the iliac artery on the side of insertion. Such an application also requires conventional femoro-femoral arterial bypass to restore continuity of the circulation to the contralateral limb and the insertion of an occlusive umbrella to prevent retrograde flow through the contralateral common iliac artery into the aneurysm. FIG. 19 is a longitudinal cross-sectional view of an occlusive umbrella 80. The graft 82 is open proximally, but closed distally, forming an inverted picket 86, which is capped by a blunt tip dilator 90. A barbed spring assembly 88 expands the open end of the graft 82. An umbrella catheter 110 having a longitudinal bore is attached to the inside of the dilator 90 and extends through the central axis of the umbrella 80. A pusher catheter 95 is abutted against the umbrella catheter 110 so that the longitudinal openings 111 and 112 are in alignment. A central pusher wire 93 is inserted through the longitudinal opening 112 of the pusher catheter 95 and through the longitudinal opening 111 of the umbrella catheter 110 until the central pusher wire 93 rests against the blunt tip dilator 90.

Figure 20:
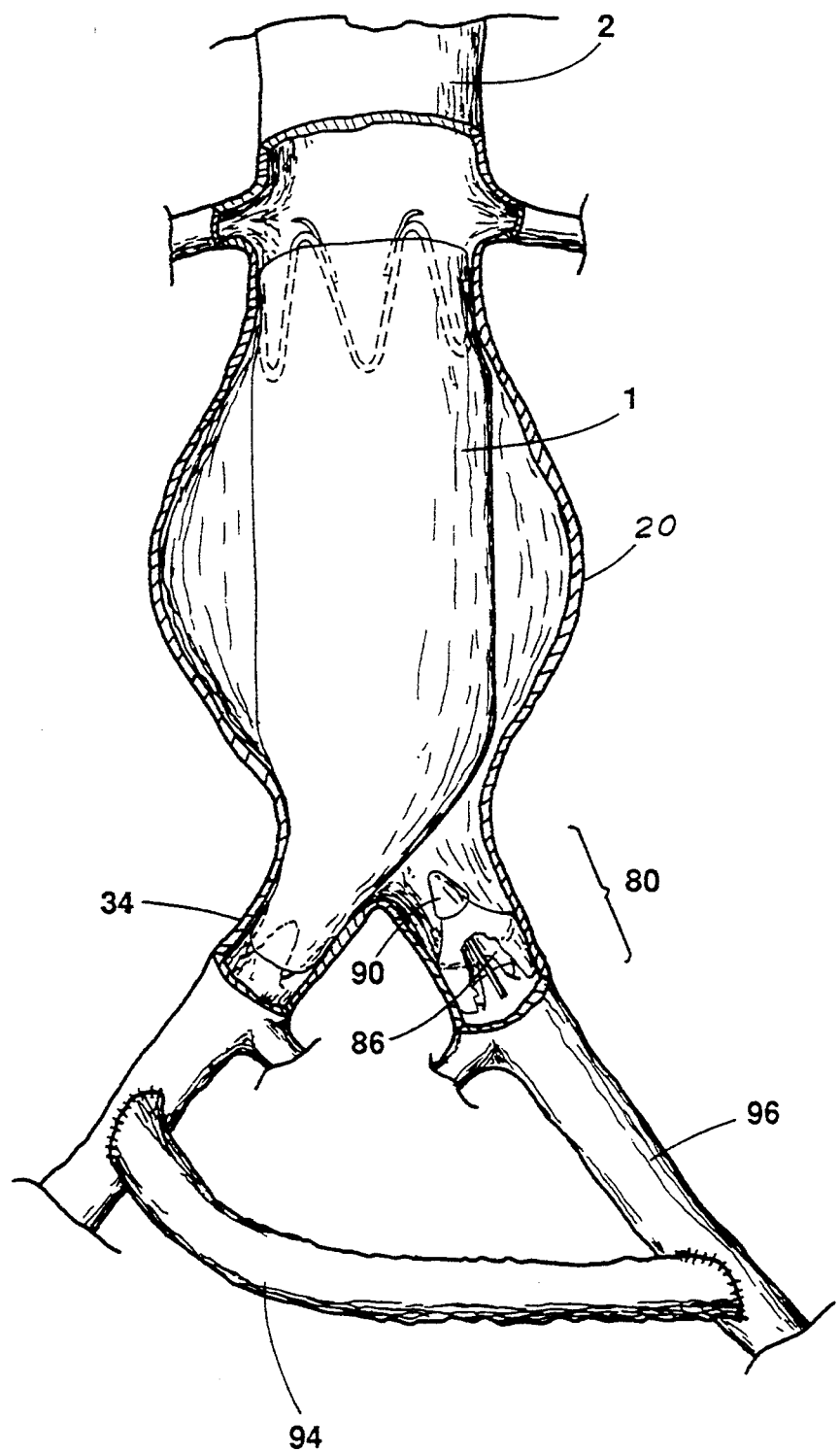
FIG. 20 is a longitudinal cross-sectional view of the aorta and the iliac arteries showing the use of a graft in conjunction with an occlusive umbrella and a femoro-femoral graft.

FIG. 20 shows an aneurysm 20 that extends from the aorta 2 to an iliac artery 34. The graft 1 is inserted so that it forms a conduit from the aorta 2 to the iliac artery 34. A conventional femoro-femoral bypass graft 94 is used to convey blood from the side receiving the entire aortic blood flow through the proximal end of the graft to the other limb. The occlusive umbrella 80 prevents arterial blood (which enters the iliac artery 34 via the femoro-femoral bypass 94) from "backing up" into the area between the graft 1 and the aneurysm 20.

Prior to insertion, the occlusive umbrella 80 is squeezed into the distal (upstream) end of the introducer sheath 4, until the introducer sheath 4 engages the blunt tip dilator 90 and the umbrella catheter 110 meets the pusher catheter 95. The umbrella catheter 110 and the pusher catheter 95 are kept in alignment by the central pusher wire 93 inserted through longitudinal openings 111 and 112. The apparatus is introduced into the femoral artery 30 through a longitudinal arteriotomy and advanced into the common iliac artery 34. The pusher 95 passes through the lumen of a flexible, thin walled, introducer sheath 4. The occlusive umbrella 80 is extruded from the introducer sheath 4 by applying force to the pusher 95 and central pusher wire 93 while pulling on the introducer sheath 4. Once the springs 88 and hooks 92 are out of the confines of the introducer sheath 4 they expand onto the arterial wall securing the umbrella 80. The pusher catheter 95, pusher wire 93, and introducer sheath 4 are then withdrawn from the femoral artery 30 through the arteriotomy. The arteriotomy is then anastomosed to the distal end of the femoro-femoral bypass 94.

When a "breech loading" introducer sheath is used, the sheath must first be inserted (over a dilator) through the femoral artery to the proximal end of the aneurysm. This can be done percutaneously or via an arteriotomy in the isolated femoral artery. The dilator is then removed, the sheath clamped, and the graft inserted. The graft is forced down the introducer sheath by a control catheter, wire or rod, which may traverse the lumen of the graft and attach the distal end of the graft to the control device or may end bluntly at the lower end of the graft. The latter requires that the graft be sufficiently rigid to withstand the compression necessary to overcome the considerable friction between the sheath and the graft.

Hereinafter described is a bifurcated endovascular graft 150 and the method of insertion thereof for repair of abdominal aortic aneurysm. Bifurcated graft insertion system 160 comprises prosthesis 170 (graft/stent combination), prosthesis delivery system 186, distal limb control system 190, distal stent insertion device 140, distal limb straightening device 130, and twist preventing catheter 120. Many features of the introducer system and the prosthesis are to be found in the various embodiments of the tubular graft insertion system. The others are unique to the bifurcated graft.

The prosthesis comprises a graft and one or more stents. Stents occupy the lumen of the graft orifices. Stents expand the graft and fix it in position.

Figure 21:
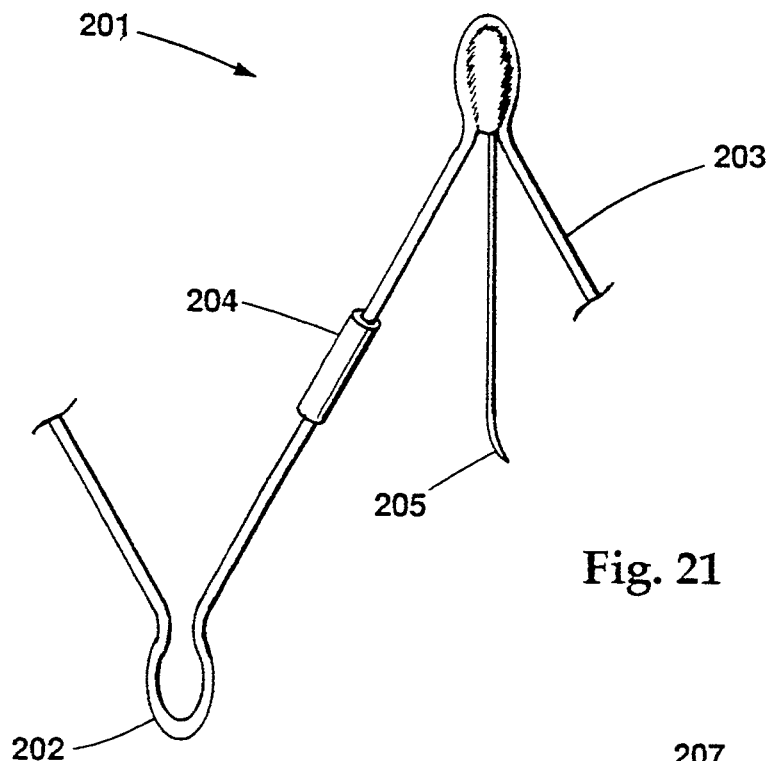
FIG. 21 depicts a segment of a self-expanding stent.

All stents are of the self-expanding (Gianturco) type of which a segment 201 is depicted in FIG. 21. A complete loop of wire is bent back and forth to form a crown or wheel with recurred points 202 between straight limbs 203. The length and number of limbs vary depending on the materials, the size of the vessel to be grafted, and the size constraints of the introducer system. However, the resting (non-deformed) diameter of a stent always exceeds the diameter of the vessels to be grafted. Cranial stents are attached to the graft. Bends, protrusions or other surface irregularities on the stents are used as a point of attachment 204. Protrusions may take the form of catheters or wires, which may be glued, soldered, or brazed to the stent. All cranial stents bear barbs 205. These sharp metal barbs project outward from the surface of the stent. The barb points caudally, cranially, or in both directions. They are soldered, brazed or glued to a stent at any point. The number of barbs is variable. Caudal stents are used with and without barbs.

Figure 22:
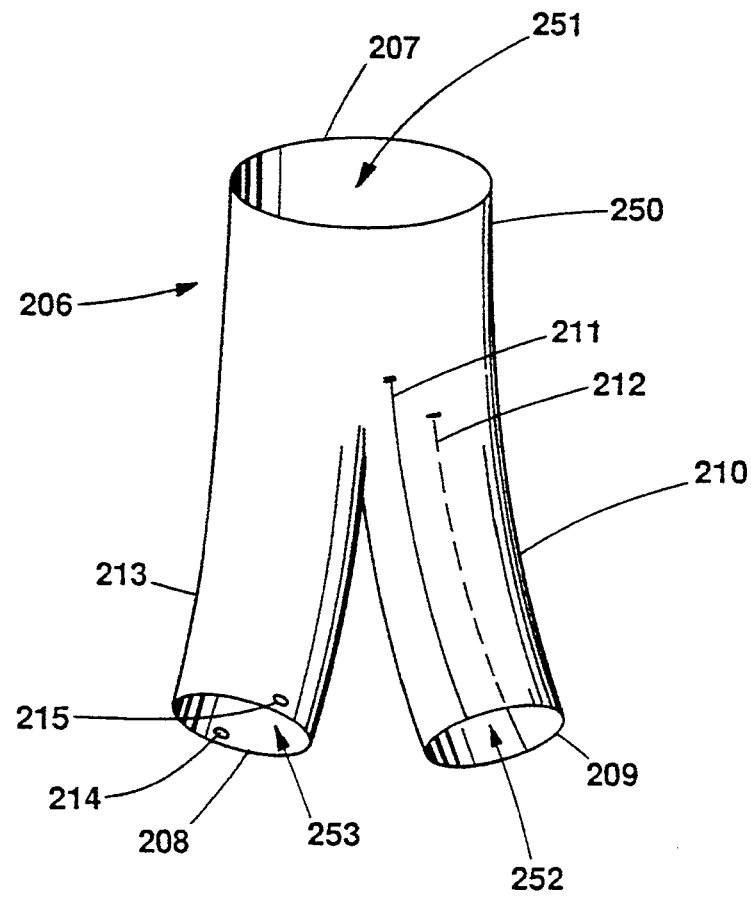
FIG. 22 depicts a bifurcated graft.

Depicted in FIG. 22 is bifurcated graft 206 having a cranial orifice 207 and at least two caudal orifices 208 and 209. The graft resembles trousers. The graft includes a main body 250 and caudal limbs 210 and 213 extending therefrom. Main body 250 includes main bore 251 extending longitudinally therein and having cranial orifice 207. Caudal limb 210 includes bore 252 extending longitudinally therein, communicating with main bore 251, and having caudal orifice 209. Caudal limb 213 includes bore 253 extending longitudinally therein, communicating with main bore 251, and having caudal orifice 208.

Grafts are knitted or woven in one piece from a durable yarn such as polyester. There are no seams. An element of elasticity may be incorporated as a property of the fabric or by subsequent treatments such as crimping. The dimensions of the graft vary according to the dimensions of the infra-renal aorta and the common iliac arteries. In each patient a graft will be selected that has diameters that exceed those of the recipient vessels.

In the majority of cases it is important to preserve blood flow through the internal iliac arteries. Therefore, most grafts will be of such a length that caudal orifices 208 and 209 lie in the common iliac arteries. An alternative embodiment uses grafts that extend through the entire common and external iliac arteries to exit the arterial tree via the femoral arteries. The caudal limb of such a graft may be perforated or constructed of very porous material to permit continued perfusion of the internal iliac artery by leakage.

Contralateral graft limb 210 on the side opposite to the side of insertion is marked with radio-opaque lines or imageable markers 211 and 212. These lines are woven into the cloth of the graft or applied after weaving. The lines may be continuous or interrupted. These lines or markers need be only imageable with any commercially available medical imaging equipment such as x-rays, CT, MRI, or the like. The radio-opaque line is a fine wire or chain of inert metal. Alternatively, the line is incorporated into an inert paint or plastic. The ipsilateral graft limb 213 needs only at least two radio-opaque markers 214 and 215 at caudal orifice 208.

Prosthesis delivery system 180 comprises central carrier 216 and co-axial introducer sheath 217. The introducer sheath has a constant diameter and wall thickness. The internal diameter of the sheath corresponds to the external diameter of the central carrier along two regions. One region is located caudally at carrier shaft 218, and the other region is located cranially at carrier head 219. In between these two regions is much narrower carrier stem region 220.

Figure 25:
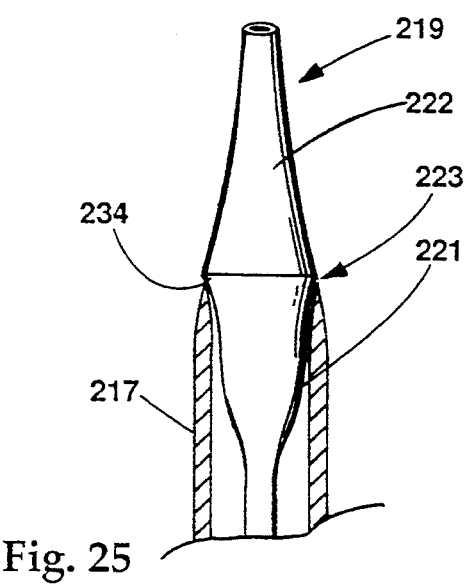
Figure 26:
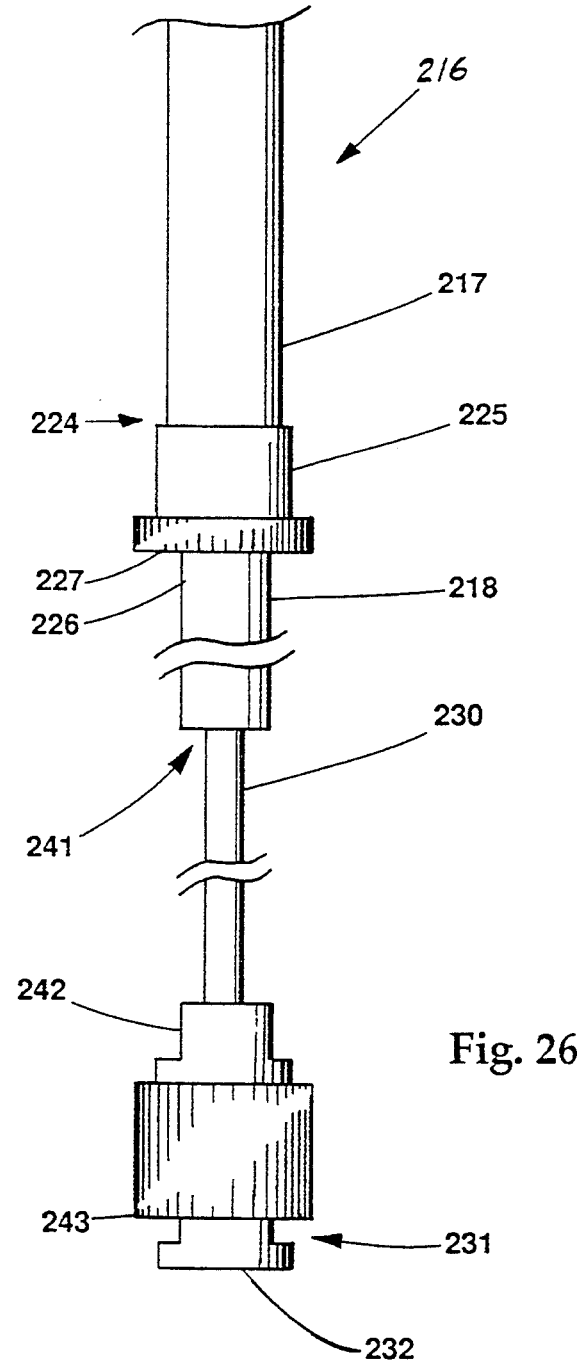

The introducer sheath is a thin-walled, large-bore catheter made of flexible, inert plastic with a low coefficient of friction. The wall of the sheath incorporates mechanisms to resist kinking (such as an internal wrap of metal wire). The sheath is of constant diameter and wall thickness, except at cranial orifice 223 where external surface 221 of the sheath tapers to meet outer surface 222 of carrier head 219 in a smooth transition as depicted in the preferred and alternative embodiments of FIGS. 24 and 25. Caudal end 224 of the sheath as depicted in FIG. 26 includes a hemostatic seal 225, which engages outer surface 226 of the carrier shaft 218. The seal incorporates a well-known lock 227 to grip the carrier shaft 226 tightly during introduction and prevent premature exposure of prosthesis 228. The length of the sheath depends on the length of the central carrier. The sheath must cover the entire carrier stem and overlap portions of the carrier head and the carrier shaft.

Figure 24:
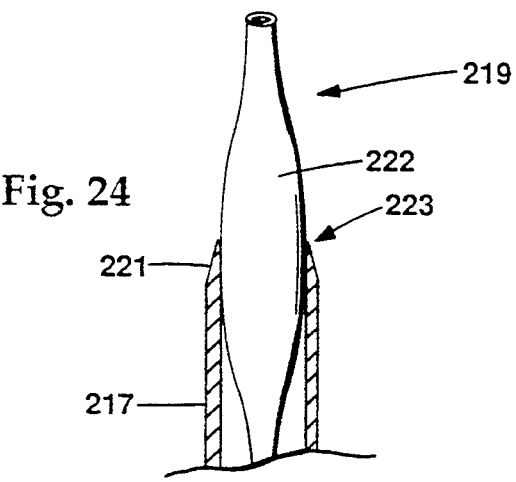
FIGS. 24 and 25 depict alternative embodiments of a sheath with a tapered cranial external surface.

As depicted in FIGS. 26 and 27, central carrier 216 includes inner catheter 229 and a co-axial outer catheter 230. The inner catheter is of constant diameter and wall thickness. Caudal end 231 of the inner catheter has an injection port 232. Outer catheter 230 has a more complicated construction. Internal lumen 233 matches the outer diameter of inner catheter 229, but the outer diameter of the outer catheter varies. Distally, the outer diameter corresponds to the inner diameter of the introducer sheath as depicted in the embodiment of FIG. 24. This segment of the outer catheter is carrier head 219. Another small dilation 234 as depicted in FIG. 25 is immediately distal to the end of introducer sheath 217, to further enhance the smooth transition from carrier head 219 to sheath 217.

The internal diameter of the introducer sheath about the caudal end thereof also matches the external diameter of the caudal segment of carrier shaft 218. The narrower segment of the central carrier between carrier head 219 and carrier shaft 218 is carrier stem 220. During insertion, prosthesis 228 and its associated catheter systems are compressed into the space between introducer sheath 217 and carrier stem 220.

Figure 23:
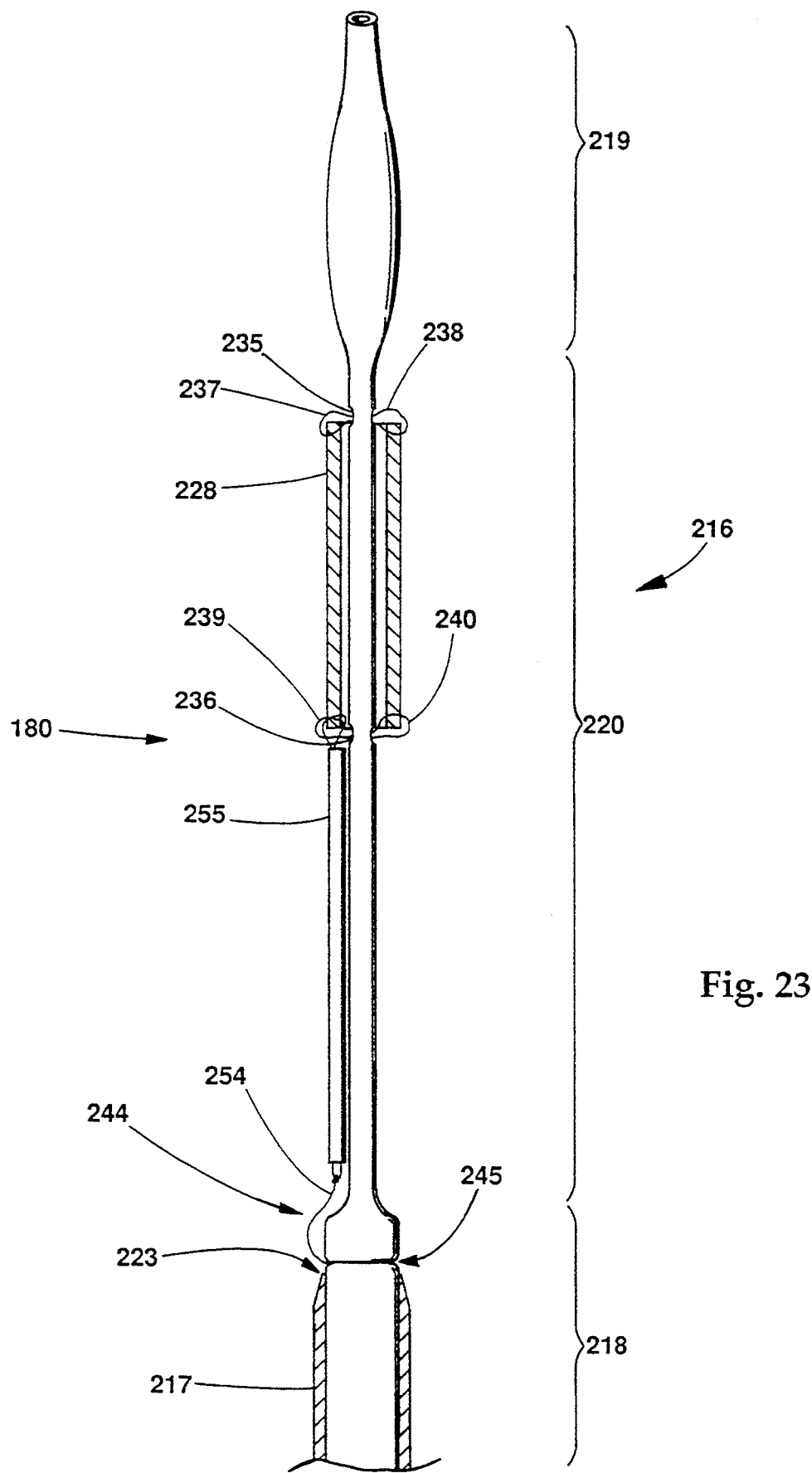
FIG. 23 depicts a carrier of the present invention.

As depicted in FIG. 23, two pairs of holes 235 and 236 traverse the outer catheter of the carrier stem, one pair at each end of prosthesis 228. As depicted in FIG. 27, small loops of suture 237 and 238 wind around inner catheter 229 at this point, entering and exiting the lumen of outer catheter 230 through the holes. These sutures, as well as suture loops 239 and 240, also traverse some part of prosthesis 228, thereby attaching both ends of the prosthesis to the central carrier. Loops 237–240 (and the prosthesis) are released by removal of inner catheter 229. It is important that the two loops of each set do not cross, otherwise the resulting linkage will prevent release from the central carrier despite removal of the inner catheter.

As depicted in FIG. 26, caudal end 241 of inner and outer catheters 229 and 230 has a short flexible extension (with dimensions and structure similar to carrier stem 220). Both inner and outer catheters have injection ports 232 and 242, respectively, at the caudal end of this extension. The injection ports may be locked together with well-known lock 243 to prevent premature removal of the inner catheter.

As depicted in FIG. 23, cranial end 244 of the carrier shaft (or the caudal end of carrier stem 220) includes annular groove 245 for attachment of the catheters and sutures.

The diameter of carrier head 219 and shaft 218 are determined by the diameter of introducer sheath 217, which in turn is dictated by the volume of the prosthesis. The minimum length of the carrier stem is the distance from the proximal end of the aneurysm to the skin of the groin. The maximum length of the carrier shaft is the length of the introducer sheath (which must exceed the length of the carrier stem). Therefore, central carrier 216 is at least twice as long as the iliac artery and aneurysm combined.

The mechanisms of caudal limb control will now be described. All caudal limb control mechanisms extend from caudal ends of limbs 210 and 213 of graft 206 to the level of the skin. Caudal limb control mechanisms take the form of detachable tubular extensions 246 and 247 of the graft as depicted in FIGS. 28 and 29, or, alternatively, combinations of catheters and/or sutures as depicted in FIGS. 32–35. Both mechanisms must be amenable to controlled release from the graft by manipulations of the caudal end thereof which extends outside the body.

As depicted in FIG. 28, tubular extensions 246 and 247 are sutured to the respective caudal ends of limbs 213 and 210 of graft 206 by chain stitches 248 and 249, which unravel when cut. These chain stitches are anchored by respective locking stitches 250 and 251. An alternative mechanism depicted in FIG. 29 involves loops of suture 252 and 253 that pass along the wall of respective tubular extensions 246 and 247 to the junction with graft 206.

Figure 30:
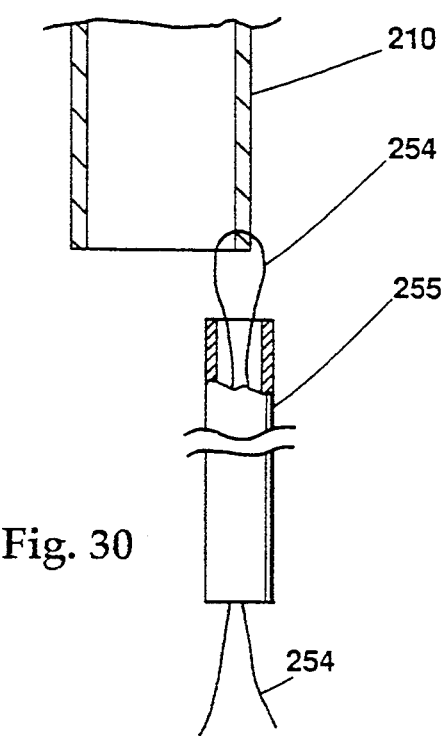
FIG. 30 depicts a single loop of suture material for applying traction to a caudal limb of the present invention.
Figure 31:
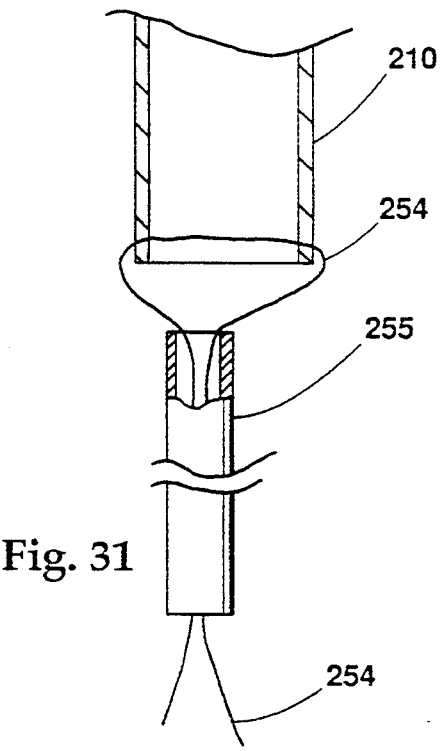
FIG. 31 depicts attachment to multiple points on a caudal limb of the present invention.
Figure 32:
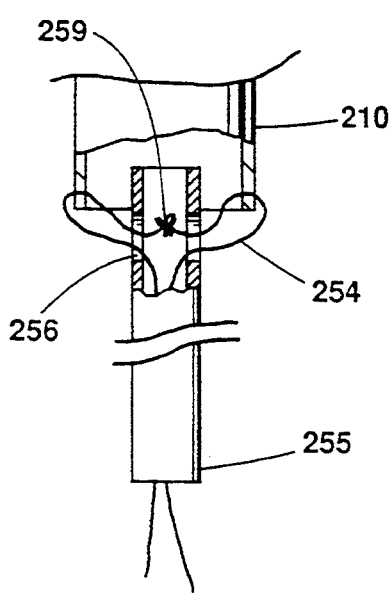
FIGS. 32 and 33 depict catheter side ports for allowing traction to be applied at multiple points.
Figure 33:
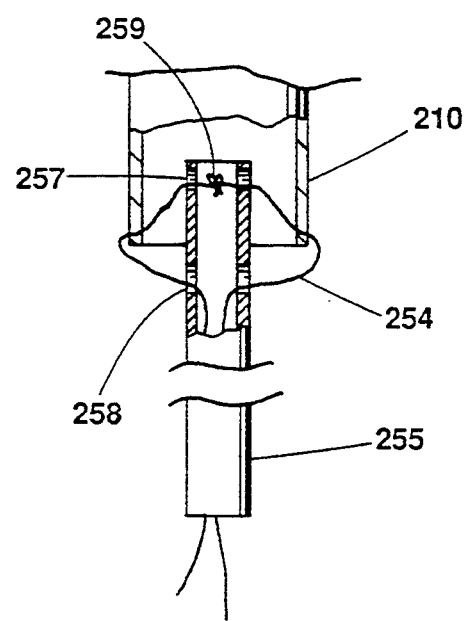
Figure 34:
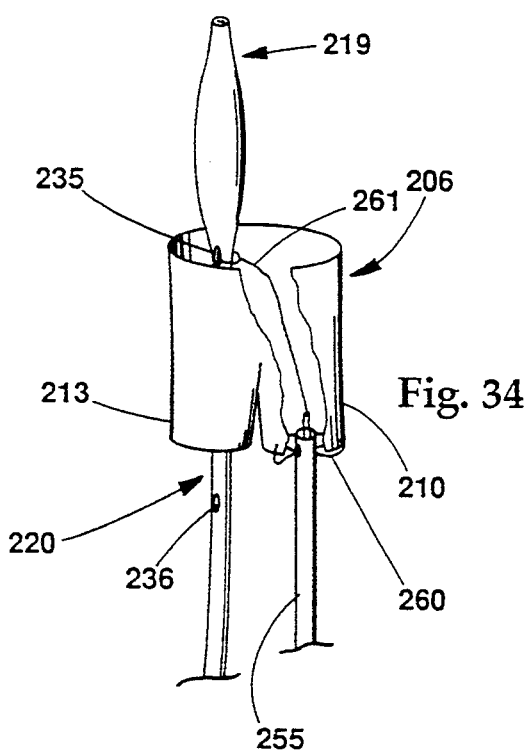
FIG. 34 depicts tension transmitted through a short suture.

Alternatively, as depicted in FIG. 30, a single loop of suture material 254 is used as the primary means of applying traction to one point on the end of the caudal limb 210. Attachment to multiple points on the end of caudal limb 210 is depicted in FIG. 31. When the one side of caudal limb control suture 154 is cut, traction on the other side pulls the end of the suture through the graft and out of the body. Enclosing the suture in catheter 255 reduces the chances of inadvertent tangling. Side ports 256 on catheter 255 in FIG. 32 and multiple side ports 257 and 258 on catheter 255 in FIG. 33 allow traction to be applied to more then one point on the graft without necessarily approximating the wall of limb 210. Knot 259 ensures that suture 254 comes out with catheter 255 when the ends are freed by dividing both sides of the loop. Catheter/suture combinations can also serve more than one function, because the tension is only transmitted through shortest suture 260 as depicted in FIG. 34. Traction on catheter 255 does not tighten suture 261 until suture 260 is cut.

Figure 35:
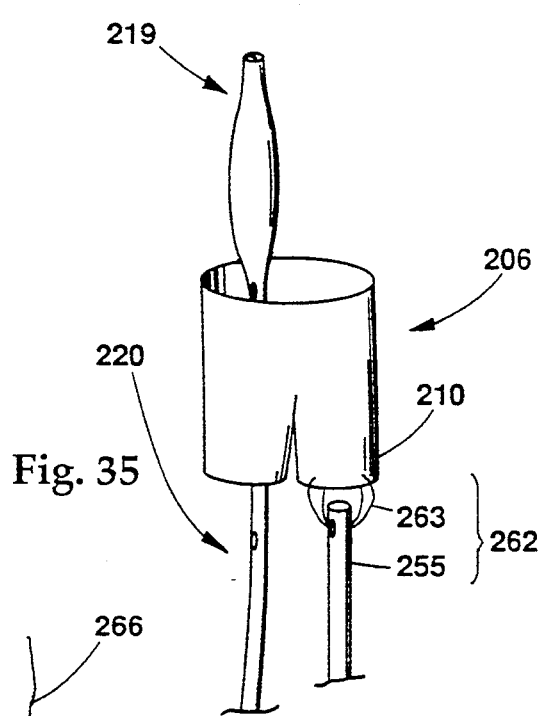
FIGS. 35 and 36 depict a caudal limb control catheter of the caudal limb control system of the present invention.

However, the two functions of limb control and guided access to the graft lumen can only be performed simultaneously if they are performed by separate catheters. FIG. 35 depicts caudal limb control catheter 255 of contralateral limb 210. Caudal limb control system 262 includes catheter 255 and suture 263.

Figure 37:
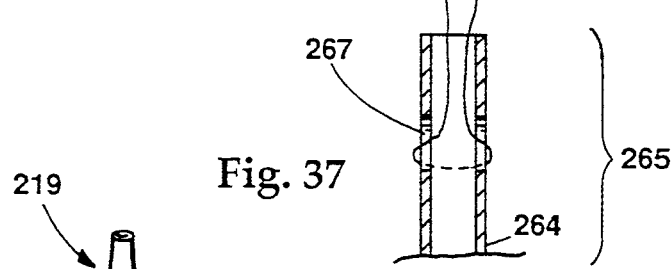
FIG. 37 depicts a suture encircling a catheter of the contralateral lumen access guidance system.
Figure 36:
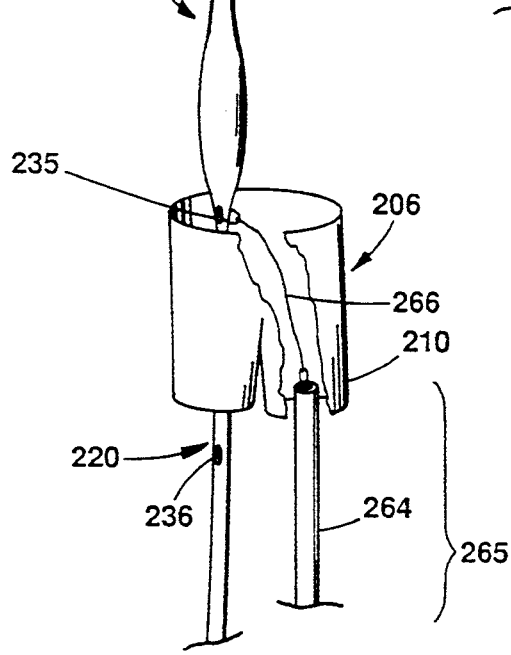
Figures 39, 42:
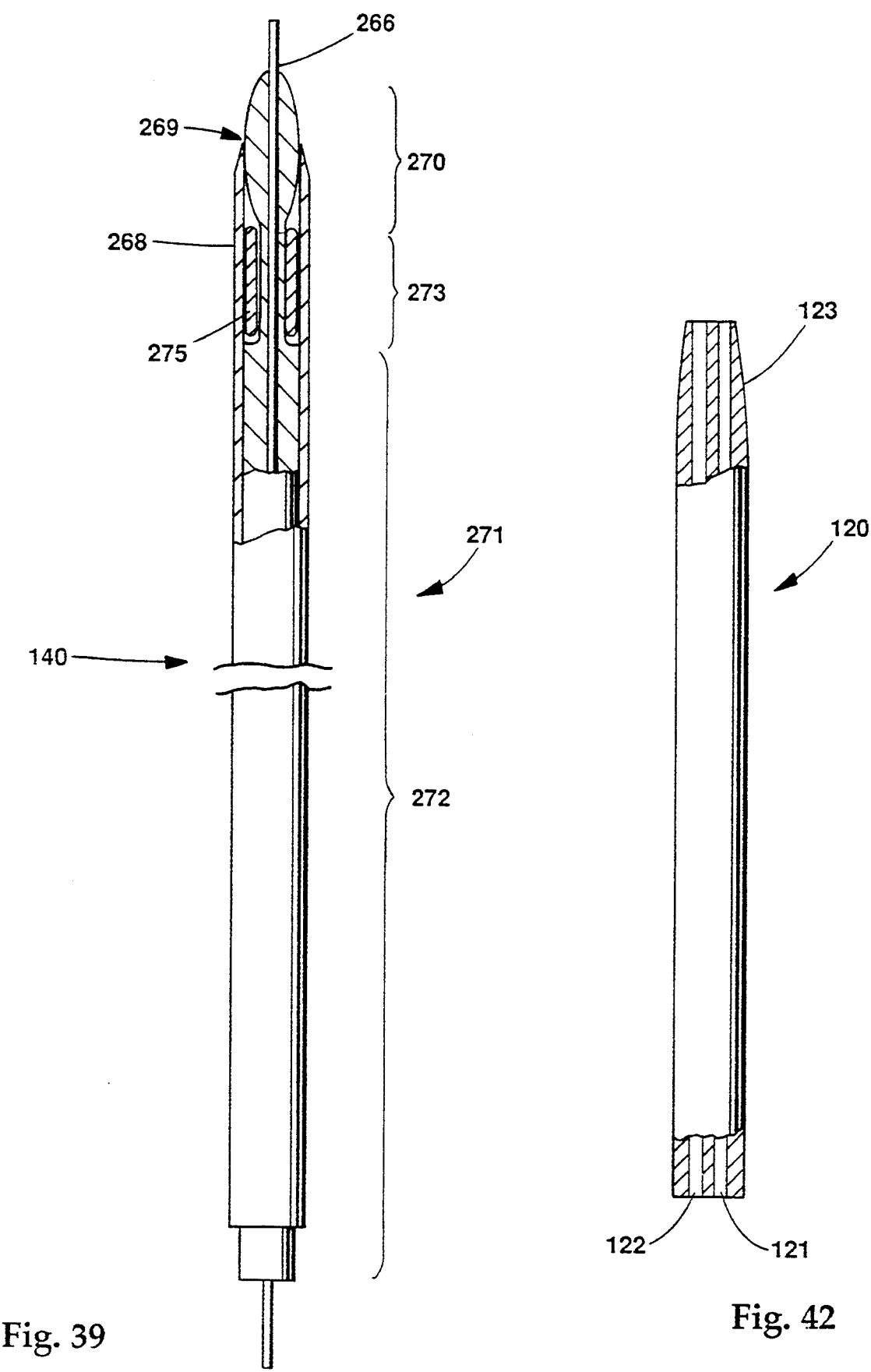
FIG. 39 depicts a distal stent insertion device of the present invention.
FIG. 42 depicts a sectioned view of a twist-preventing, double lumen catheter.

As depicted in FIG. 36, guided access to the caudal lumen of contralateral limb 210 is provided by a catheter 264 which is moored to the central carrier in the same manner as loops 237 and 238 on the prosthesis. Contralateral lumen access guidance system 265 becomes tense and inflexible when traction is applied to its outer end. When tense, it functions as a guide wire within the lumen of the stent insertion device 140 as depicted in FIG. 39. Contralateral limb access guidance system 265 is released from central carrier 216 when inner catheter 229 is removed. Mooring loop 266 is attached to the end of the catheter or passes through its lumen to the caudal end (where a knot prevents suture retraction). Sutures that are tied through side holes 267 in the catheter have a tendency to pull out when tension is applied unless the suture also encircles part of the catheter to distribute traction more evenly as depicted in FIG. 37.

Figure 38:
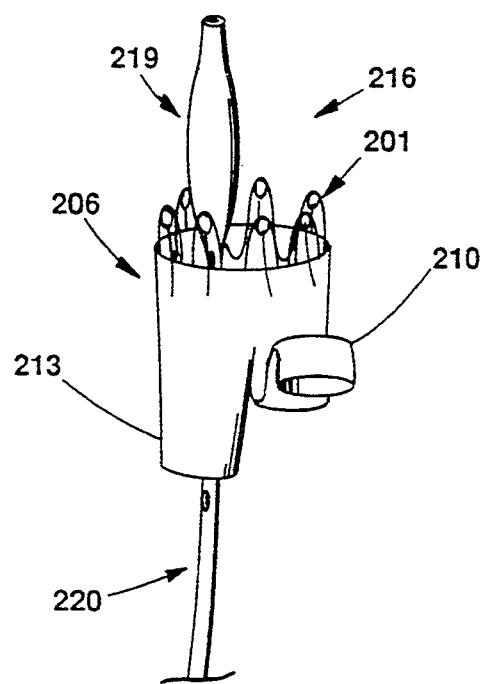
FIG. 38 depicts access to the ipsilateral limb lumen by an insertion delivery wire.

As depicted in FIG. 38, access to the lumen of the ipsilateral limb 213 is guided by the same wire that is used for angiography and for insertion of the delivery system. If traction is to be maintained during insertion of a stent on the ipsilateral side, a caudal limb control catheter 255 is also required on ipsilateral distal limb 213.

The orientation of the contralateral limb (and associated catheters) to the carrier must be constant, because any twists are subsequently reproduced in the relative orientation of the two distal limbs. As an additional precaution, the location of contralateral limb 210 is marked on the outside of the delivery system.

Catheters may be made of any plastic that is flexible yet strong enough to hold sutures with extreme thin-walled construction. All sutures should be strong yet fine enough to pass through small catheters. They should also have a low coefficient of friction, to enhance removal at the end of the procedure. Many monofilament and coated multifilament sutures satisfy these criteria. Catheters must be long enough to be accessible at the groin when the contralateral limb has been pulled into position.

Depicted in FIG. 39 is caudal stent insertion device 140 including stent pusher 271 and outer sheath 268. The basic structure and function of the caudal stent insertion device is similar to prosthesis delivery system 180.

Caudal stent insertion device introducer sheath 268 is of constant diameter and wall thickness, except at cranial orifice 269 where the external surface of the sheath tapers to meet the surface of pusher head 270 in a smooth transition. The sheath is made of flexible, inert plastic with a low coefficient of friction. The wall of the sheath may incorporate mechanisms to resist kinking (such as an internal wrap of metal wire). At the cranial end of stent pusher 271 is pusher head 270, which has an external diameter that matches the internal diameter of the introducer sheath. Pusher shaft 272 also matches the diameter of the introducer sheath. Between the two is a narrow pusher stem 273, which passes through the center of caudal stent 275.

Depicted in FIG. 40 is contralateral limb straightening device 130 for orienting the position of contralateral limb 210 of graft 206. Translocation of the contralateral limb of the bifurcated graft can produce twists. Straightening device 130 is advanced over the distal limb control system onto the end of the distal limb and rotated to remove twists. The contralateral limb straightening device is a catheter or small gauge dilator with a fish-mouth split at cranial end 274. The terminal split occupies a plane that also contains the long axis of the device. When traction is applied to suture 254 of the contralateral distal limb control system, the suture is pulled into the catheter approximating the two walls of the graft. The flattened contralateral limb then slides into the slot of the advancing straightening device. Torsion on the device is transmitted to the end of the graft to straighten any twists.

Figure 41:
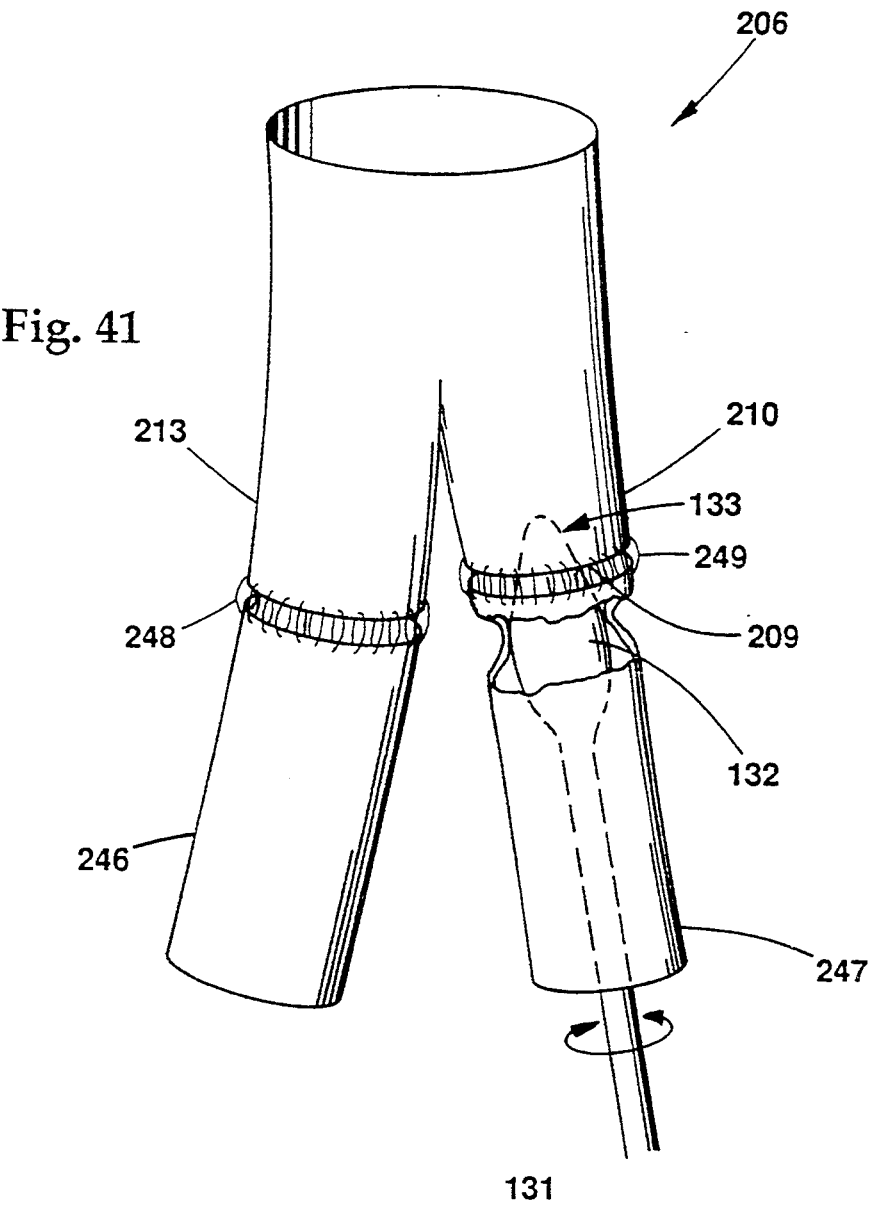
FIG. 41 depicts an alternative limb straightening device.

Depicted in FIG. 41 is an alternative limb straightening device 131 designed primarily for use with the system of tubular graft extensions 246 and 247. The alternative device is a dilator with a soft rounded tip and a bulbous dilation 132 at cranial end 133. The dilatation is pushed into a narrowing of the tubular extension, which is maintained under tension by traction on the caudal end. The tight fit enables torsional forces to be transmitted to the graft through friction at the surface of the dilatation. In the absence of the tubular graft extensions, the alternative limb straightening device is advanced over contralateral lumen access guidance system 265. The dilatation then engages the inner aspect of the distal limb orifice 209. Alternatively, the dilatation may take the form of a balloon, which is inflated inside caudal limb 210. Whatever form the straightener takes, it must be long enough to reach the end of the caudal limb from the femoral arteriotomy. The diameter is variable, depending on the mechanism of graft attachment. The device must be flexible, yet resist deformation when torsional stresses are applied to the caudal end.

Depicted in FIG. 42 is a sectioned view twist-preventing, double lumen catheter 120. This soft, flexible catheter has two lumens 121 and 122. One is occupied by the cross femoral catheter, while the other is occupied by the angiographic catheter (or wire). Cranial end 123 is slightly tapered for ease of insertion. The catheter resists torsion so that the relative orientation of the two lumens is maintained. The twist-preventing, double lumen catheter is inserted to the point where the two catheters diverge, one passing through the aneurysm to the proximal aorta, the other crossing to the opposite iliac artery.

The method for inserting the prosthesis and use of the insertion instruments is hereinafter described. Patients are selected for this procedure on the basis of radiographic imaging (including angiography) and general physical condition.

The patient is placed in the supine position on a radiolucent operating table. Access to the arterial tree may be obtained by surgical isolation of the femoral vessels in the groin. Alternatively, the insertion may be performed through large introducer sheaths placed by percutaneous techniques. In the open technique, silastic bands around the common femoral arteries provide proximal hemostasis, while non-crushing clamps provide distal hemostasis. Most patients will be anticoagulated with heparin prior to the interruption of the circulation to the legs.

Insertion is guided by fluoroscopy. When available, digital subtraction processing enhances fluoroscopic images and is used to record angiograms. Another useful feature of digital subtraction imaging equipment is the "roadmapping" function, which combine real time fluoroscopic images with static angiograms. The composite image facilitates guidance of the apparatus through the vascular tree.

An initial angiogram is performed to provide the reference points that guide insertion. Angiography will frequently have been performed as part of the selection procedure, in which case measurements determining graft size and form will already have been taken. After initial angiography the catheter is removed, leaving the guide wire in place.

A wire, suture, catheter or tape is passed from one femoral artery to the other. In one method depicted in FIGS. 48 and 49, a Dormier basket 280 is passed up the ipsilateral femoral artery 30 and opened over the contralateral iliac artery orifice 281. A catheter or guide wire 282 is threaded up the opposite femoral artery 96 through the wires of the Dormier basket. The basket is then closed on the guide wire and withdrawn pulling the guide wire through femoral access site 283. The procedure is swift and relatively atraumatic, especially if a very soft, flexible catheter is used. An alternative method involves fluoroscopically guided manipulation of the curved tip of a catheter/guide wire system from one iliac artery into the other.

Care must be taken to avoid winding the angiographic catheter around the cross femoral system. This may be accomplished by inserting the angiographic catheter (or wire) through one lumen of a double lumen, twist-preventing catheter 120 as depicted in FIG. 42, while the other lumen is occupied by the cross femoral system (or vice versa).

The introducer system is threaded over the same guide wire that occupied the lumen of the angiographic catheter. Fluoroscopic visualization is relatively easy because all components of the apparatus (except the fabric of the graft) are radio-opaque. The position of the prosthesis is controlled during extrusion by manipulation of the central carrier. When the introducer sheath is withdrawn, the stents expand, opening the graft and fixing it in position. Further withdrawal of the introducer sheath 217 exposes the caudal limb control mechanisms and their attachment to central carrier 216. The caudal limb control mechanisms, such as suture loops 237 and 238 or other catheters, sutures, or tubular graft extensions, are attached to the cross femoral system (catheter, suture, tape or guide wire) using sutures, tape or clips. Traction on the cross femoral system (at the contralateral groin) pulls the contralateral limb 210 into the contralateral iliac artery.

The contralateral limb 210 is sometimes twisted after translocation to the contralateral iliac artery. Twisting is revealed by the fluoroscopic appearance of the radio-opaque lines 211 and 212. The contralateral limb control mechanism such as suture loops 237 and 238 is used to apply traction to other contralateral limb 210 and pull it onto the advancing contralateral limb straightening device 130 or 131. Straightening is guided by the fluoroscopic appearance and the character of the femoral arterial pulse and blood flow.

Stents are occasionally required to prevent retrograde leakage of blood around the caudal limbs 210 and 211 back into the aneurysm. The distal stent insertion device may be passed through the lumen of a tubular graft extension 247. Alternatively, the stent insertion device is passed over a guide wire or over contralateral lumen access guidance system 265. Whichever method is used, it is usually necessary to maintain traction on the caudal limbs using the caudal limb control mechanism. Insertion of the ipsilateral stent cannot be performed until the delivery system has been removed.

The prosthesis 228 is released from the central carrier 216 by removal of the inner catheter 229. It is important to replace the inner catheter and advance the guide wire through the central lumen before removing the delivery system, because the wire is needed to guide the stent insertion device into the lumen of the ipsilateral caudal limb 213. After stent insertion the wire is needed again to guide insertion of a catheter for completion angiography. If angiographic appearances are satisfactory, the catheters are removed, the arteries repaired, and the wounds closed.

Figure 43:
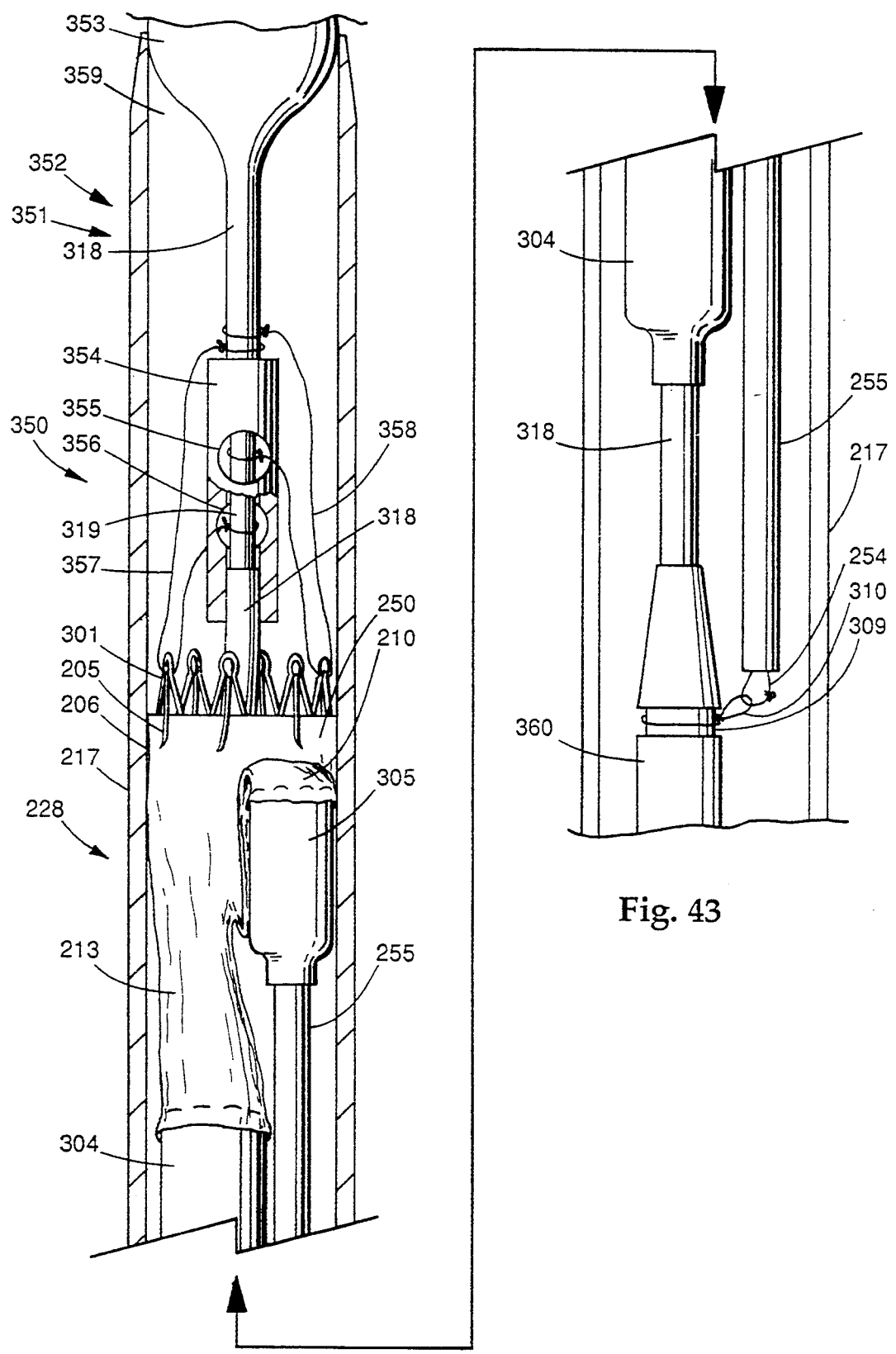
FIG. 43 depicts a partially sectioned view of a transluminal arrangement of the present invention for positioning a prosthesis assembly at a particular position in a bifurcated lumen.
Figure 48:
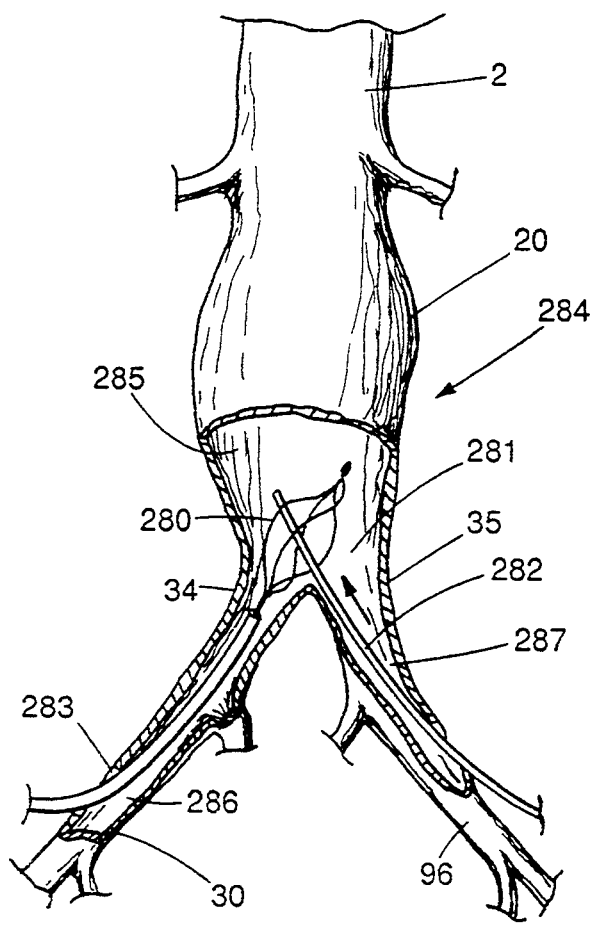
FIGS. 48 and 49 depict the method of deploying a cross femoral wire guide between femoral access sites positioned on opposite sides of the groin.
Figure 49:
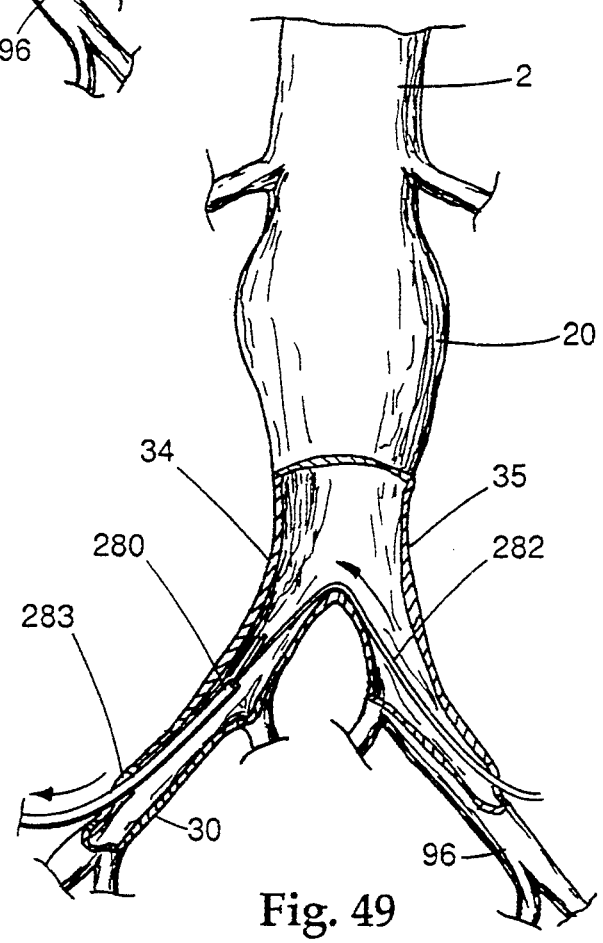

Depicted in FIG. 43 is transluminal arrangement 350 for positioning prosthesis assembly 228 at a particular position in a bifurcated lumen. As depicted in FIGS. 48 and 49, bifurcated lumen 284 is located in aorta 2 with common iliac arteries 34 and 35 extending distally therefrom. Aortic aneurysm 20 is located just proximal the common iliac arteries 34 and 35. Aortic lumen 285 forms the main lumen, whereas common iliac lumens 286 and 287 communicating with the main lumen form the branch lumens.

Prosthesis assembly 228 depicted in FIG. 43 includes bifurcated endovascular graft 206, main spring assembly 301, and limb spring assemblies 302 and 303 (not shown) positioned in respective stent boots 304 and 305. Main spring assembly 301, as well as prosthesis assembly 228, is contained in main container sheath 217 which is, for example, a polytetrafluoroethylene tube. Bifurcated endovascular graft 206 includes main body 250 with ipsilateral limb 213 and contralateral limb 210 extending therefrom and partially over the tops of respective stent boots 304 and 305.

As previously described with respect to FIG. 22, main body 250 includes main bore 251 extending longitudinally therein with cranial orifice 207. Contralateral limb bore 252 and ipsilateral limb bore 253 communicate with main bore 251 and extend longitudinally through respective contralateral limb 210 and ipsilateral limb 213. Contralateral limb 210 has caudal orifice 209, whereas ipsilateral limb 213 has caudal orifice 208. Main spring assembly 301 is positioned through cranial orifice 207 and into bore 251 of the main body for radially expanding the main body of the graft to substantially conform the main body of the graft on the interior wall of main lumen 285. Main spring assembly 301 expands from its compressed state, as shown in FIG. 43, when the prosthesis assembly is positioned in the bifurcated lumen and released from container sheath 217.

Transluminal arrangement 350 includes outer sheath 217 for containing main spring assembly 301 in a compressed state, stent boot sheath 304 for containing ipsilateral spring assembly in a compressed state; stent boot sheath 305 for containing contralateral spring assembly in a compressed state; and main retainer assembly 351 positioned in the main and ipsilateral bores of the graft for retaining prosthesis assembly 228 in the bifurcated lumen while the outer sheath is withdrawn from the prosthesis assembly releasing the main spring assembly from its compressed state.

Similar to previously described central carrier 216, main retainer assembly comprises elongated member 352 having dilator head 353 at the distal end thereof. The dilator head serves to facilitate penetration of the transluminal arrangement within the bifurcated lumen and minimizes deleterious blood flow during positioning of the transluminal arrangement. Elongated member 352 also includes an intermediate carrier stem region including outer catheter 318, hollow connector sleeve 354 with lateral apertures 355 and 356 formed therein, and inner catheter 319 extending longitudinally through the elongated member including the outer catheter and connector sleeve. Connector sleeve 354 interconnects segments of outer catheter 318 and facilitates as to permit attachment of sutures 357 and 358 to inner catheter 319 through respective apertures 355 and 356. One end of attachment sutures 357 and 358 are tied around the outer surface of outer catheter 318, whereas other end of the sutures are tied around the outer surface of inner catheter 319 through the connector sleeve apertures. Attachment sutures 357 and 358 are looped through the opposite sides of main spring assembly 301 for retaining the prosthesis assembly in the bifurcated lumen while outer sheath 217 is withdrawn from the prosthesis assembly releasing the main spring assembly from its compressed state. The outer sheath includes longitudinal bore 359 in which the prosthesis assembly is positioned during insertion of the assembly into the bifurcated lumen. Attachment sutures 357 and 358 form a contraction assembly for temporarily pulling main spring assembly 301 to a compressed state when prosthesis assembly 228 is positioned within main outer sheath 217. The distal end of the outer sheath is positioned next to the proximal end of dilator head 353 to facilitate easy insertion of the transluminal arrangement into the bifurcated lumen.

Elongated member 352 also includes a carrier shaft region 360 similar to carrier shaft region 218 of which annular recess 309 is formed therein.

FIG. 44 depicts a partially sectioned side view of ipsilateral limb spring assembly 302 in a compressed state. The spring assembly is attached to the inside of ipsilateral limb 213 via sutures 315 and 316 and is contained in stent boot sheath 304. When the prosthesis assembly is properly positioned about aneurysm 20, ipsilateral spring assembly 302 is released from its compressed state to radially expand limb 213 and substantially conform the limb to the interior wall of common iliac artery 34. Stent boot sheath 304 forms a container for containing ipsilateral spring assembly 302 in a compressed state. Suture 314 is temporarily attached to ipsilateral spring assembly 302 for retaining the spring assembly in the stent boot sheath during positioning of the prosthesis assembly in the bifurcated lumen. Suture 314 forms a release mechanism for releasing the ipsilateral spring assembly when the prosthesis assembly is positioned in the bifurcated lumen and, in particular, when ipsilateral limb 213 is properly positioned in common iliac artery 34. After suture 314 is detached from the ipsilateral spring assembly, stent boot 304 is withdrawn from the spring assembly, releasing it from its compressed state. When released from its compressed state, ipsilateral spring assembly 302 radially expands graft limb 213 to substantially conform the limb on an interior wall of iliac artery lumen 286.

Stent boot 304 is a tubular container such as a sheath or short piece of polytetrafluoroethylene tube for containing ipsilateral spring assembly 302 therein in a compressed state. Ipsilateral spring assembly 302 is attached along its midsection to contralateral graft limb 213 inside limb bore 253 with sutures 315 and 316. Attachment sutures 315 and 316 are placed cranially from caudal orifice 208 to allow the caudal end of the graft limb to extend over the top of stent boot 304. Attachment sutures 314 and 317 are temporarily attached to ipsilateral spring assembly 302 for retaining the spring assembly in stent boot 304. One end of attachment sutures 314 and 317 are tied around outer catheter 318 of the transluminal positioning arrangement, whereas the other end of the sutures are tied around inner catheter 319 through apertures 320 and 321 of connector sleeve 322. The inner catheter of the positioning arrangement forms part of a release mechanism that is temporarily attached to the ipsilateral spring assembly for releasing attachment sutures 314 and 317. Attachment sutures 314 and 317 and inner catheter 319 form a retainer mechanism for retaining ipsilateral spring assembly 302 in stent boot 304. Connector sleeve 322 is a short length of tubing having apertures 320 and 319 formed laterally therethrough. The connector sleeve has an inner diameter approximating the outer diameter of outer catheter 318. Outer catheter 318 is cut and inserted into the opposite ends of the connector sleeve and bonded thereto using, for example, medical grade adhesive. Inner catheter 319 passes through the passageway of the connector sleeve and outer catheter for retaining attachment sutures through the lateral apertures in the sleeve.

FIG. 45 depicts a partially sectioned side view of contralateral spring assembly 304, attached to the inside of contralateral limb 210, and contained in stent boot 305. Limb control catheter 255 is attached proximally to stent boot 305 and has suture 254 extending longitudinally through catheter lumen 306. Suture 254 is temporarily attached to contralateral spring assembly for retaining the spring assembly in the stent boot during positioning of the prosthesis assembly in the bifurcated lumen. Suture 254 forms a release mechanism for releasing the contralateral spring assembly when the prosthesis assembly is positioned in the bifurcated lumen and, in particular, when contralateral limb 210 is positioned in common iliac artery 35. After suture 254 is detached from the contralateral spring assembly, stent boot 305 is withdrawn from the spring assembly, releasing it from its compressed state. When released from its compressed state, contralateral spring assembly 303 radially expands limb 210 to substantially conform the limb on an interior wall of iliac artery lumen 287. Limb control catheter 255 is a commercially available copolymer tube to which stent boot 305 is integrally formed or attached thereto, for example, using medical grade adhesive. Stent boot 305 is a tubular container such as a short piece of polytetrafluoroethylene tube for containing contralateral spring assembly 303 therein in a compressed state. Contralateral spring assembly 303 is attached along its midsection to contralateral graft limb 210 inside limb bore 255 with sutures 307 and 308. Attachment sutures 307 and 308 are placed cranially from caudal orifice 209 to allow the caudal end of the graft limb to extend over the top of stent boot 305. Contralateral spring assembly 303 can include one or more barbs for digging into the vessel wall and more securely anchoring the prosthesis assembly. However, the contralateral spring assembly can be used with or without these barbs. Retainer suture 254 is temporarily attached to carrier shaft annular recess 309 via suture 310.

Figure 46:
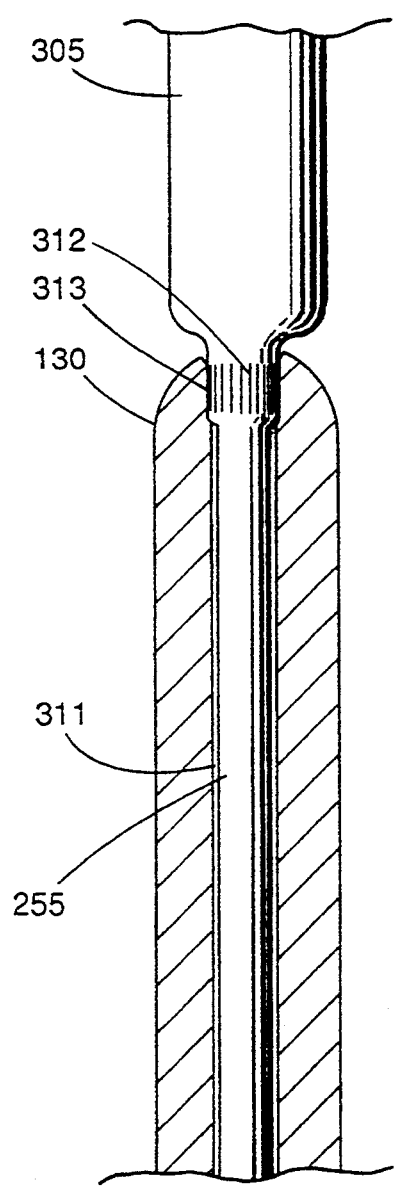
FIG. 46 depicts a partially sectioned side view of contralateral stent boot temporarily attached to control limb delivery catheter of FIG. 45.

FIG. 46 depicts a partially sectioned side view of stent boot 305 attached to control limb delivery catheter 255 which is positioned in longitudinal lumen 311 of contralateral limb straightening device 130. A plurality of longitudinal splines 312 is formed in the proximal end of stent boot 305 to match a corresponding plurality of splines 313 positioned around the distal end of straightening device lumen 311. The mating splines engage each other to rotate the stent boot and contralateral limb for proper positioning within the common iliac artery. Markers are positioned in the graft limbs for radiographic imaging.

Figure 47:
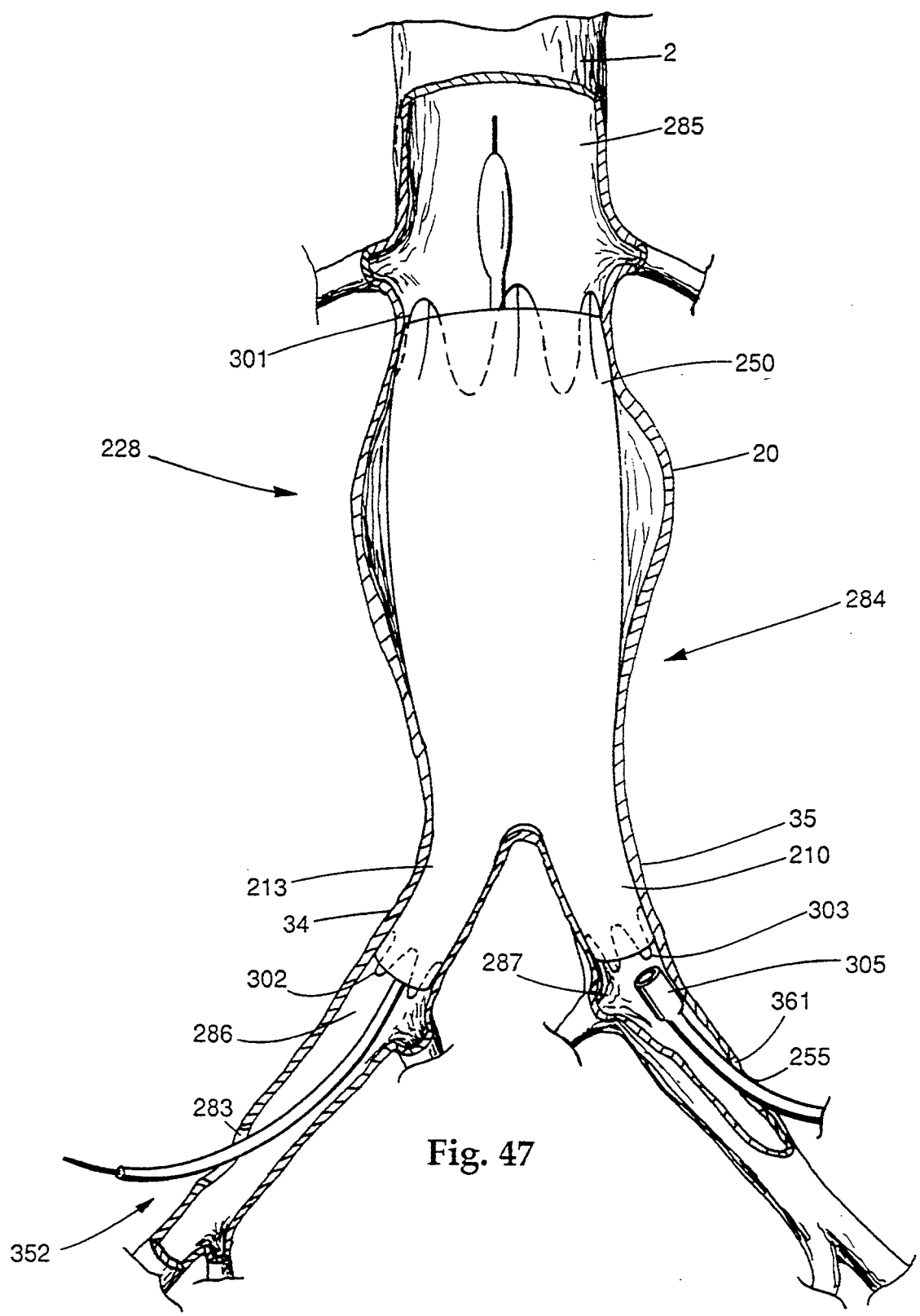
FIG. 47 depicts a prosthesis assembly of the present invention positioned in the bifurcated lumen of the aorta and common iliac arteries extending therefrom.

FIG. 47 depicts prosthesis assembly 228 positioned in bifurcated lumen 284 of aorta 2 and common iliac arteries 34 and 35. Main spring assembly 301 has been released from its compressed state and radially expanded main body 250 of the graft to substantially conform the main body of the graft on the interior wall of main lumen 285 of the aorta. Similarly, ipsilateral spring assembly 302 has been released from its compressed state and elongated member 352 and radially expanded ipsilateral limb 213 of the graft to substantially conform the ipsilateral limb on an interior wall of lumen 286 of common iliac artery 34. Contralateral spring assembly 303 has been released from its compressed state and radially expanded contralateral limb 210 to substantially conform the contralateral limb of the graft on an interior wall of lumen 287 of common iliac artery 35. Control limb delivery catheter 255 and stent boot 305 have been withdrawn from the contralateral spring assembly allowing it to expand the contralateral limb of the graft.

The method of positioning the prosthesis assembly at the particular position in bifurcated lumen 284 includes providing first and second access sites 283 and 361 to branch lumens 286 and 287 in respective common iliac arteries 34 and 35 in a well-known manner. As previously described with respect to FIGS. 48 and 49, the guide is provided between access sites 283 and 361 via the branch lumens. Transluminal arrangement 350 including retainer assembly 351, elongated member 352, and prosthesis assembly 228 attached thereto are positioned within the bifurcated lumen. Outer sleeve 217 is withdrawn from the prosthesis assembly, and control limb delivery catheter 255 guides the contralateral limb of the graft into branch lumen 287 of iliac artery 35. The attachment sutures are released from the main, ipsilateral and contralateral spring assemblies positioning the prosthesis in the bifurcated lumen. Stent boots 304 and 305 are removed from their respective spring assemblies during withdrawal of retainer assembly 352 and control limb delivery catheter 255.

The transluminal arrangement for positioning a prosthesis assembly at a particular position in a bifurcated lumen and the method of placement has been illustrated and described in the drawing and the foregoing description, the same is to be considered illustrative and not restrictive in character. It is to be understood that only the preferred embodiment has been shown and that all changes and modifications that come within the scope of the claims are to be protected. In particular, stent boots 304 and 305 have been referred to as containers or sheaths and are typically formed from a thin polytetrafluoroethylene tube of material. The stent boots are either affixed to the outer catheter of the retainer assembly or slidable thereon. Similarly, stent boot 304 is attached using, for example, medical grade adhesive, are slidable at the end of the control delivery catheter. Outer sheath 217 is also a container or sheath of, for example, a semi-rigid polytetrafluoroethylene material for containing the prosthesis assembly therein. The spring assemblies are of the Gianturco Z-stent type as previously described with or without barbs for more securely affixing the prosthesis assembly to the wall of the bifurcated lumen. Any type of radially expanding spring assembly or stent is contemplated whether the spring assembly or stent is automatically expanded when released from a container or expanded with a dilator balloon and the like.

What is claimed is:

1. A transluminal arrangement comprising:
main container means containing in a compressed state a main spring assembly of a prosthesis assembly, said prosthesis assembly including a bifurcated endovascular graft having a main body and a first and a second limb extending therefrom, said main body including a main bore extending longitudinally therein and having a cranial orifice, said first limb including a first bore extending longitudinally therein, communicating with said main bore, and having a first caudal orifice, said second limb including a second bore extending longitudinally therein, communicating with said main bore and having a second caudal orifice, said main spring assembly radially expanding said main body of said graft to substantially conform said main body of said graft on an interior wall of a main lumen of a bifurcated lumen when said prosthesis assembly is positioned at a particular position in the bifurcated lumen and said main spring assembly is released from said compressed state, the bifurcated lumen including the main lumen and a first and a second branch lumen communicating with and extending from the main lumen;

first container means separated from said main container means containing in a compressed state a first spring assembly of said prosthesis assembly, said first spring assembly radially expanding said first limb of said graft to substantially conform said first limb of said graft on an interior wall of the first branch lumen of the bifurcated lumen when said prosthesis assembly is positioned at the particular position in the bifurcated lumen and said first spring assembly is released from said compressed state;

retainer means positioned in said main and said first bore of said graft for retaining said prosthesis assembly at the particular position in the bifurcated lumen while said main container means is withdrawn from said prosthesis assembly releasing said main spring assembly from said compressed state.

2. The transluminal arrangement of claim 1 wherein said main container means includes a main sheath having a longitudinal bore and wherein said prosthesis assembly is positioned within said bore of said main sheath.

3. The transluminal arrangement of claim 1 wherein said retainer means comprises an elongated member having a dilator head at a distal end thereof, said head serving to facilitate penetration of said arrangement within the bifurcated lumen and to minimize deleterious blood flow through the bifurcated lumen during positioning of said arrangement.

4. The transluminal arrangement of claim 3 wherein said first container means includes a first sheath having a longitudinal bore and attached around said elongated member caudally from said dilator head and wherein said first spring assembly is positioned in said bore of said first sheath.

5. The transluminal arrangement of claim 1 wherein said retainer means comprises main attachment means for temporarily attaching said main spring assembly to said retainer means when said prosthesis assembly is being positioned at the particular position in the bifurcated lumen.

6. The transluminal arrangement of claim 5 wherein said retainer means comprises first attachment means for temporarily attaching said first spring assembly to said retainer means when said prosthesis assembly is being positioned at the particular position in the bifurcated lumen.

7. The transluminal arrangement of claim 6 wherein said main and said first attachment means comprises contraction means for temporarily pulling respectively said main and said first spring assembly inwardly to said compressed state when said prosthesis assembly is positioned within said main sheath.

8. The transluminal arrangement of claim 6 wherein said main and said first attachment means comprises release means for releasing said prosthesis assembly from said retainer means either during or after removal of at least one of said main and said first sheath.

9. The transluminal arrangement of claim 8 wherein at least one of said main and said first attachment means comprises one or more sutures connected to at least one of said main and said first spring assembly and at one end to inside of said retainer means via apertures therein, and wherein said release means is positioned within said retainer means for releasing said suture from inside said retainer means.

10. A transluminal arrangement for positioning a prosthesis assembly at a particular position in a bifurcated lumen, the bifurcated lumen including a main lumen and a first and a second branch lumen communicating with and extending from the main lumen, said prosthesis assembly including a bifurcated endovascular graft having a main body and a first and a second limb extending therefrom, said main body including a main bore extending longitudinally therein and having a cranial orifice, said first limb including a first bore extending longitudinally therein, communicating with said main bore, and having a first caudal orifice, said second limb including a second bore extending longitudinally therein, communicating with said main bore and having a second caudal orifice, said assembly including a main spring assembly, a first spring assembly, and a second spring assembly each having a compressed state, said main spring assembly radially expanding said main body of said graft to substantially conform said main body of said graft on an interior wall of the main lumen when said prosthesis assembly is positioned at a particular position in the bifurcated lumen and said main spring assembly is released from said compressed state, said first spring assembly radially expanding said first limb of said graft to substantially conform said first limb of said graft on an interior wall of the first branch lumen when said prosthesis assembly is positioned at the particular position in the bifurcated lumen and said first spring assembly is released from said compressed state, said second spring assembly radially expanding said second limb of said graft to substantially conform said second limb of said graft on an interior wall of the second branch lumen when said prosthesis assembly is positioned at a particular position in the bifurcated lumen and said second spring assembly is released from said compressed state, said transluminal arrangement comprising:

main container means for containing said main spring assembly in said compressed state;

first container means for containing said first spring assembly in said compressed state;

second container means for containing said second spring assembly in said compressed state;

main retainer means positioned in said main and said first bore of said graft for retaining said prosthesis assembly at the particular position in the bifurcated lumen while said main container means is withdrawn from said prosthesis assembly releasing said main spring assembly from said compressed state;

first retainer means temporarily attached to said first spring assembly for retaining said first spring assembly in said first container means; and second retainer means temporarily attached to said second spring assembly for retaining said second spring assembly in said second container means.

11. The transluminal arrangement of claim 10 wherein said main container means includes a main sheath with a longitudinal bore and wherein said prosthesis assembly is positioned in said bore of said main sheath.

12. The transluminal arrangement of claim 10 wherein said first container means includes a first sheath with a longitudinal bore and wherein said first spring assembly is positioned in said bore of said first sheath.

13. The transluminal arrangement of claim 10 wherein said second container means includes a second sheath with a longitudinal bore and wherein said second spring assembly is positioned in said second bore of said second sheath.

14. The transluminal arrangement of claim 10 wherein said main retainer means comprises an elongated member having a dilator head at a distal end thereof, main attachment means for temporarily attaching said main spring assembly to said elongated member, and first attachment means for temporarily attaching said first spring assembly to said elongated member.

15. The transluminal arrangement of claim 14 further comprising first release means for releasing at least one of said main and said first attachment means either during or after removal of at least one of said main and said first container means.

16. The transluminal arrangement of claim 15 further comprising second release means temporarily attached to said second spring assembly for releasing said second spring assembly when positioned in the second branch of the bifurcated lumen.

17. A transluminal arrangement for positioning a prosthesis assembly at a particular position in a bifurcated lumen, the bifurcated lumen including a main lumen and a first and a second branch lumen communicating with and extending from the main lumen, said prosthesis assembly including a bifurcated endovascular graft having a main body and a first and a second limb extending therefrom, said main body including a main bore extending longitudinally therein and having a cranial orifice, said first limb including a first bore extending longitudinally therein, communicating with said main bore, and having a first caudal orifice, said second limb including a second bore extending longitudinally therein, communicating with said main bore and having a second caudal orifice, said graft including a main spring assembly, a first spring assembly, and a second spring assembly each having a compressed state, said main spring assembly radially expanding said main body of said graft to substantially conform said main body of said graft on an interior wall of the main lumen when said prosthesis assembly is positioned at a particular position in the bifurcated lumen and said main spring assembly is released from said compressed state, said first spring assembly radially expanding said first limb of said graft to substantially conform said first limb of said graft on an interior wall of the first branch lumen when said prosthesis assembly is positioned at the particular position in the bifurcated lumen and said first spring assembly is released from said compressed state, said second spring assembly radially expanding said second limb of said graft to substantially conform said second limb of said graft on an interior wall of the second branch lumen when said prosthesis assembly is positioned at a particular position in the bifurcated lumen and said second spring assembly is released from said compressed state, said transluminal arrangement comprising:

a main sheath with said prosthesis assembly positioned in a bore of said main sheath;

main container means for containing said main spring assembly in said compressed state;

a first sheath with said first spring assembly positioned in a bore of said first sheath;

first container means for containing said first spring assembly in said compressed state;

a second sheath with said second spring assembly positioned in a bore of said second sheath;

second container means for containing said second spring assembly in said compressed state;

an elongated member positioned in said main and said first bore of said graft;

main attachment means for temporarily attaching said main spring to said elongated member;

first attachment means for temporarily attaching said first spring to said elongated member, said main and said first attachment means for retaining said prosthesis assembly at the particular position in the bifurcated lumen while said main sheath is withdrawn from said prosthesis assembly;

first retainer means temporarily attached to said first spring assembly for retaining said first spring assembly in said first container means;

second retainer means temporarily attached to said second spring assembly for retaining said second spring assembly in said second container means;

first release means for releasing at least one of said main and said first attachment means either during or after removal of at least one of said main and said first sheath; and second release means temporarily attached to said second spring assembly for releasing said second spring assembly when positioned in the second branch lumen of the bifurcated lumen.

* * * * *

UNITED STATES PATENT AND TRADEMARK OFFICE
CERTIFICATE OF CORRECTION

PATENT NO. : 5,387,235
DATED : February 7, 1995
INVENTOR(S) : CHUTER, Timothy A.

It is certified that error appears in the above-indentified patent and that said Letters Patent is hereby corrected as shown below:

Patent Cover Page, under heading entitled Related U.S. Application Data, first line, delete "Ser. No. 868,795, Apr. 19," and replace with --Ser. No. 868,792, Apr. 15,--.

Column 1, line 9, delete "07/868,795" and replace with --07/868,792--.

Signed and Sealed this

Fifteenth Day of April, 1997

Attest:

BRUCE LEHMAN

*Attesting Officer*    *Commissioner of Patents and Trademarks*